(12) United States Patent
Kochi et al.

(10) Patent No.: US 8,300,986 B2
(45) Date of Patent: Oct. 30, 2012

(54) IMAGE MEASUREMENT APPARATUS FOR CREATING A PANORAMIC IMAGE

(75) Inventors: Nobuo Kochi, Tokyo (JP); Tetsuharu Anai, Tokyo (JP); Hitoshi Ohtani, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 1120 days.

(21) Appl. No.: 12/186,893

(22) Filed: Aug. 6, 2008

(65) Prior Publication Data

US 2009/0245653 A1  Oct. 1, 2009

(51) Int. Cl.
*G06K 9/32* (2006.01)
(52) U.S. Cl. .................... 382/299; 382/294; 382/295
(58) Field of Classification Search .............. 382/154, 382/199, 255, 275, 284, 294, 299; 348/36–39, 348/143, 218.1, 211.4; 345/419, 428
See application file for complete search history.

(56) References Cited

U.S. PATENT DOCUMENTS

| | | | | |
|---|---|---|---|---|
| 5,991,444 A * | 11/1999 | Burt et al. | ...... | 382/232 |
| 6,208,765 B1 * | 3/2001 | Bergen | ...... | 382/268 |
| 6,434,280 B1 * | 8/2002 | Peleg et al. | ...... | 382/299 |
| 7,352,919 B2 * | 4/2008 | Zhou et al. | ...... | 382/299 |
| 7,587,099 B2 * | 9/2009 | Szeliski et al. | ...... | 382/275 |
| 7,660,478 B2 * | 2/2010 | Steinberg et al. | ...... | 382/255 |
| 7,697,778 B2 * | 4/2010 | Steinberg et al. | ...... | 382/255 |
| 7,907,792 B2 * | 3/2011 | Harville | ...... | 382/284 |
| 7,916,971 B2 * | 3/2011 | Bigioi et al. | ...... | 382/275 |
| 2003/0002707 A1 * | 1/2003 | Reed et al. | ...... | 382/100 |
| 2006/0197867 A1 | 9/2006 | Johnson et al. | | |
| 2006/0244746 A1 | 11/2006 | England et al. | | |
| 2007/0064976 A1 | 3/2007 | England et al. | | |

FOREIGN PATENT DOCUMENTS

| | | |
|---|---|---|
| EP | 1 591 959 A1 | 11/2005 |
| JP | 2000-292166 A | 10/2000 |
| JP | 2002-010297 A | 1/2002 |

OTHER PUBLICATIONS

Alessandro Balsamo, Antonio Chimienti, Paolo Grattoni, Roberto Nerino, Giuseppe Pettiti, Maria Luisa Rastello, Massimiliano Spertino, Active vision applications to cultural heritage acquisition and monitoring, Journal of Cultural Heritage, vol. 7, Issue 2, Apr.-Jun. 2006, pp. 98-109.*

J. F. Canny, "A computational approach to edge detection", IEEE Transaction on Pattern Analysis and Machine Intelligence, 8(6), Nov. 1986, pp. 679-698.

(Continued)

*Primary Examiner* — Vu Le
*Assistant Examiner* — Andrae S Allison
(74) *Attorney, Agent, or Firm* — Foley & Lardner LLP

(57) ABSTRACT

A measurement processing block obtains a plurality of first images of the object to be measured, taken with very small movements in the imaging area. A feature extraction processing block extracts an approximate feature portion of the object from the first images obtained by the measurement processing block. A partial-image creation processing block creates a plurality of first partial images by grouping the plurality of first images obtained by the measurement processing block in the vicinity of the approximate feature portion extracted by the feature extraction processing block. A super-resolution-image creation processing block creates a super-resolution image from the plurality of first partial images created by the partial-image creation processing block. Thus, detailed features of the object are measured precisely and easily even when the object is located far away.

9 Claims, 27 Drawing Sheets

OTHER PUBLICATIONS

"Image Analysis Handbook", edited by Mikio Takagi and Akihisa Shimoda, University of Tokyo Press, 1991, pp. 548-561.

A. Balsamo et al., "Active vision applications to cultural heritage acquisition and monitoring", Journal of Cultural Heritage, vol. 7, No. 2, Apr. 1, 2006, pp. 98-109.

D. Capel et al., "Computer vision applied to super resolution", IEEE Signal Processing Magazine, vol. 20, No. 3, May 1, 2003, pp. 75-86.

P. Grattoni et al., "A mosaicing approach for the acquisition and representation of 3D painted surfaces for conversation and restoration purposes", Machine Vision and Applications, vol. 15, No. 1, Oct. 1, 2003, pp. 1-10.

Measurement Search Consultant, "3D Measurement Apparatus", KRC Web Report, No. 45, Dec. 26, 2006.

* cited by examiner

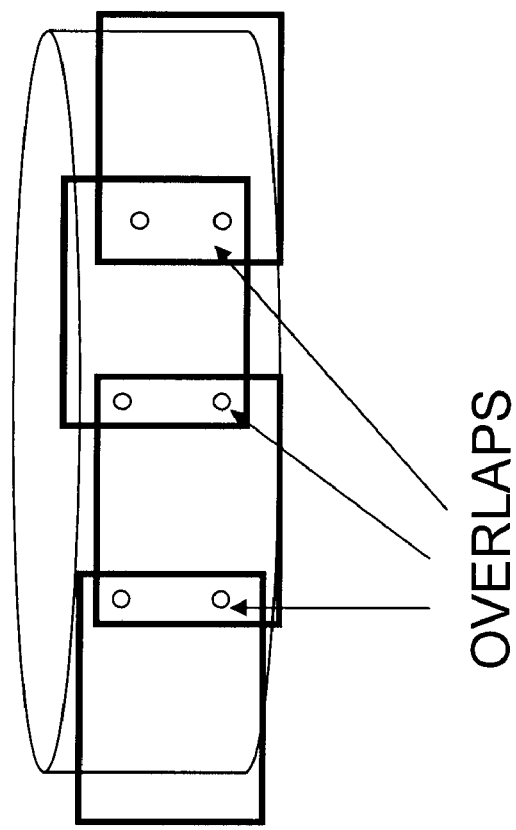

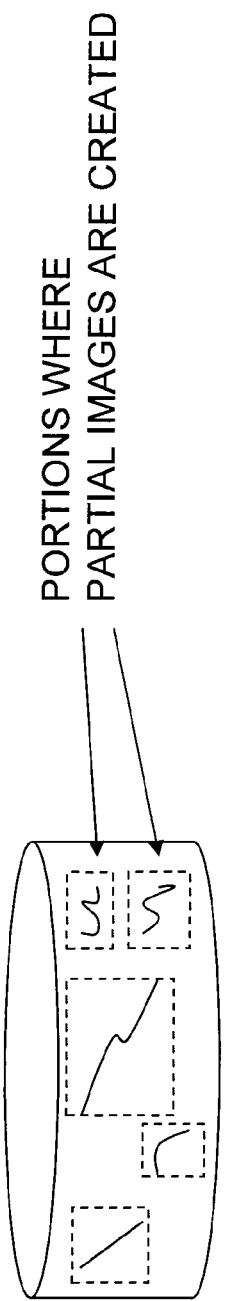

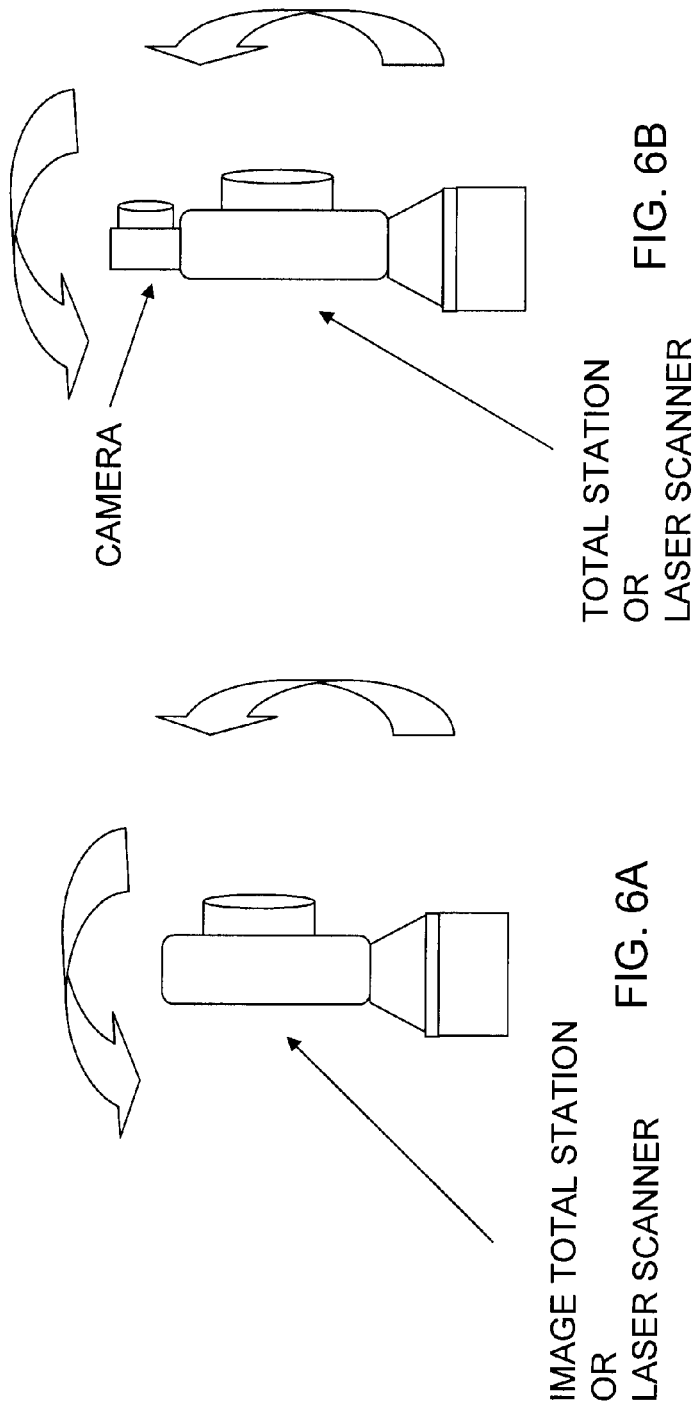

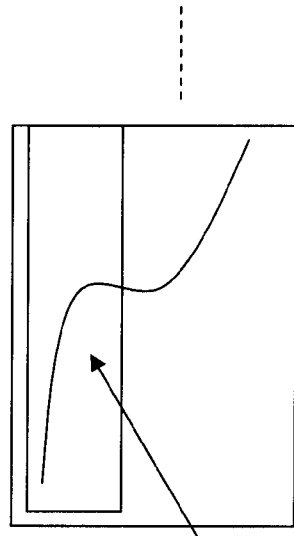
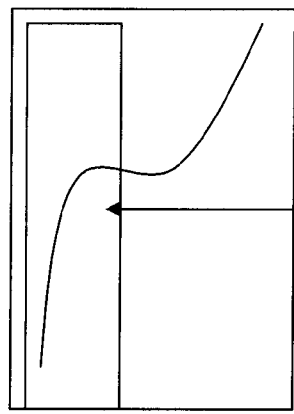
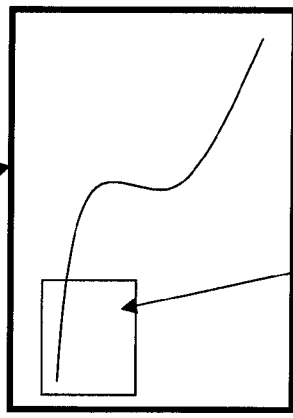
FIG. 11A REFERENCE IMAGE
CUT-OUT AREA (PARTIAL IMAGE)
TEMPLATE
FIG. 11B MICRO-MOVEMENT IMAGE
FIG. 11C MICRO-MOVEMENT IMAGE
MULTIPLE IMAGES
SEARCH AREAS

EDGE EXTRACTION | RESULT OF EDGE EXTRACTION
ORIGINAL IMAGE

| 0 | -1 | 0 |
|---|---|---|
| -1 | 5 | -1 |
| 0 | -1 | 0 |

LAPLACIAN OPERATORS

FIG. 22

| -1/2 | 1 | -1/2 |
| --- | --- | --- |
| -1/2 | 1 | -1/2 |
| -1/2 | 1 | -1/2 |

LINE DETECTION OPERATORS

FIG. 23

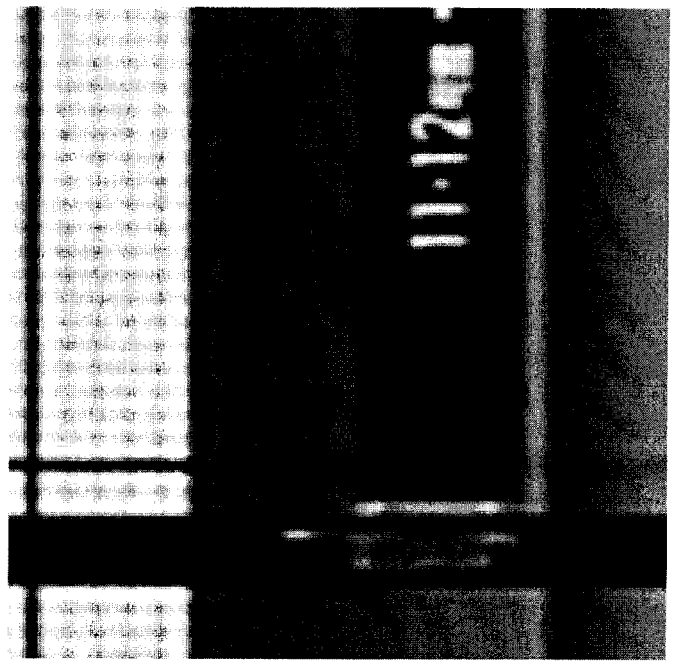
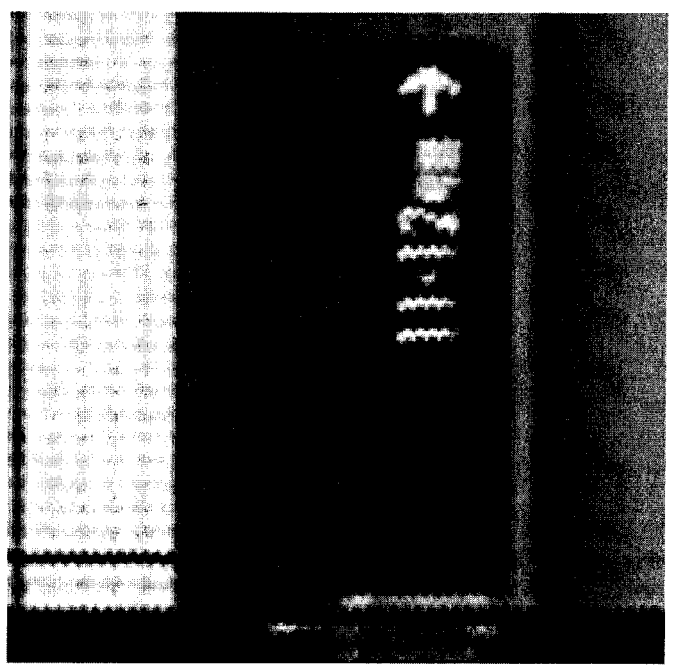
SUPER RESOLUTION FROM 16 IMAGES
BICUBIC METHOD
FIG. 25

IMAGE MEASUREMENT APPARATUS FOR CREATING A PANORAMIC IMAGE

BACKGROUND OF THE INVENTION

1. Field of the Invention

The present invention relates to image measurement apparatuses, and more specifically, to an image measurement apparatus which performs detailed, high-precision, three-dimensional measurement of a remote object to be measured.

2. Description of the Related Art

Conventionally, if a crack needs to be measured, the width of the crack is measured with a ruler (such as a crack measure), and the shape is sketched with pencil and paper.

If the object to be measured is in a high place in a smokestack or wall, scaffolding is needed in the method that uses the ruler. The measured result is drawn by hand, and the hand-drawn sketch may include a measurement error.

A measurement method that uses a non-prism total station has been developed in recent years. This method allows both measurement data and coordinates to be obtained simultaneously and also allows a three-dimensional record to be saved. A combination of a distance measuring apparatus and an angle measuring apparatus is referred to as a total station, for instance. The total station has the advantage that an unreachable place can be measured safely from a distance of 1 to 350 meters.

Japanese Unexamined Patent Application Publication No. 2000-292166 discloses an image creation apparatus that allows an image drawing (orthographic projection image: orthoimage) to be created easily while checking it on the spot in real time. Japanese Unexamined Patent Application Publication No. 2002-10297 discloses a stereo imaging system that allows a stable, highly-reliable, high-precision stereo image to be taken easily in three-dimensional measurement using an ordinary camera.

SUMMARY OF THE INVENTION

At some measurement distance or with some apparatus performance, however, the non-prism total station may not be able to measure a feature point of a crack or the like. For example, a crack having a width of 0.2 mm or greater in a concrete wall should be extracted usually because it could lead to a leakage of water, and this allows measurement from a distance of just up to 30 m because of the magnification of the telescope or the like. Measurement of bridges or in disaster-stricken areas should be made often at a distance of 30 meters or greater from the place where the total station is set up, but the remote measurement would not provide a desired resolution.

When the features of cracks or the like are measured, the positions to be measured must be determined in advance in a field survey, then the total station must be directed manually to the positions to be measured in turn, to observe each of them minutely. This work requires much time and labor. Especially in high-magnification measurement, because it narrows down the range of sight, it increases the volume of observation, and reduces efficiency.

One possible solution is to use a telescope having a higher magnification or a camera having a higher resolution. However, to produce an apparatus that can achieve a uniform resolution of 0.2 mm or greater across a wide range of 1 to 350 meters is not a good idea in terms of structure and cost. In addition, to collimate the apparatus manually to a narrow area from a remote place is quite difficult.

Crack measurement has been described as an example, but the same can be said about measurement of something other than cracks in a wall, measurement of a marked place or the like, and measurement of their long-term changes.

Accordingly, it is an object of the present invention to provide an image measurement apparatus that allows detailed features of an object to be measured easily with high precision, even if the object is in a remote place.

According to the first solving means of the present invention, there is provided an image measurement apparatus comprising:

a measurement processing block for obtaining a plurality of first images of an object to be measured, taken while very small movements are being made in an imaging area;

a feature extraction processing block for extracting an approximate feature portion of the object from the plurality of first images obtained by the measurement processing block;

a partial-image creation processing block for creating a plurality of first partial images by grouping the plurality of first images obtained by the measurement processing block in the vicinity of the approximate feature portion extracted by the feature extraction processing block; and a super-resolution-image creation processing block for creating a super-resolution image from the plurality of first partial images created by the partial-image creation processing block;

wherein the feature extraction processing block extracts a detailed feature portion from the super-resolution image.

According to the second solving means of the present invention, there is provided an image measurement apparatus comprising:

a measurement processing block for obtaining a first image of an object to be measured, taken under low magnification;

a feature extraction processing block for extracting an approximate feature portion of the object from the first image obtained by the measurement processing block; and a super-resolution-image creation processing block for creating a super-resolution image from a plurality of second images taken in the vicinity of the approximate feature portion extracted by the feature extraction processing block, while very small movements are being made in an imaging area containing the approximate feature portion, under magnification higher than that of the first image;

wherein the feature extraction processing block extracts a detailed feature portion from the super-resolution image.

The present invention produces an enormous effect of enabling a feature point to be measured automatically with high precision in three dimensions even from a remote place and the feature point to be imaged.

BRIEF DESCRIPTION OF THE DRAWINGS

FIG. 4 illustrates the creation of a panoramic image.
FIG. 5 illustrates the creation of a partial image.
FIGS. 6A to 6C show sample structures of a measuring apparatus.
FIGS. 11A to 11C illustrate templates and search areas.

FIG. 22 illustrates Laplacian operators.

FIG. 23 illustrates line detection operators.

FIG. 25 shows an example of super-resolution image actually created.

DESCRIPTION OF THE PREFERRED EMBODIMENTS

1. Apparatus Structure

Figure 1:
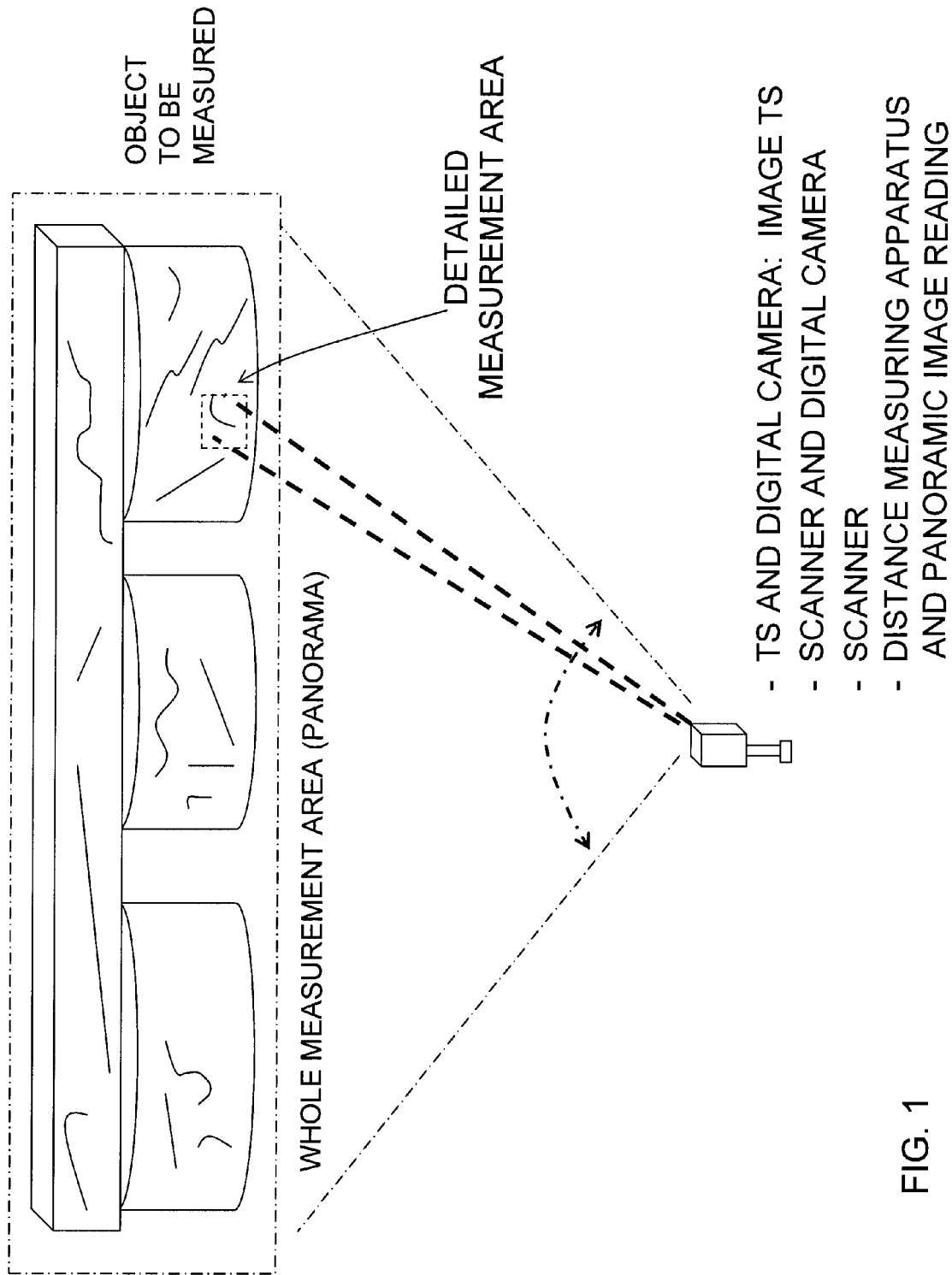
FIG. 1 illustrates image measurement.

FIG. 1 illustrates image measurement. The figure shows the whole measurement area (panorama) of an object to be measured by a measuring apparatus and a detailed measurement area.

Figure 14:
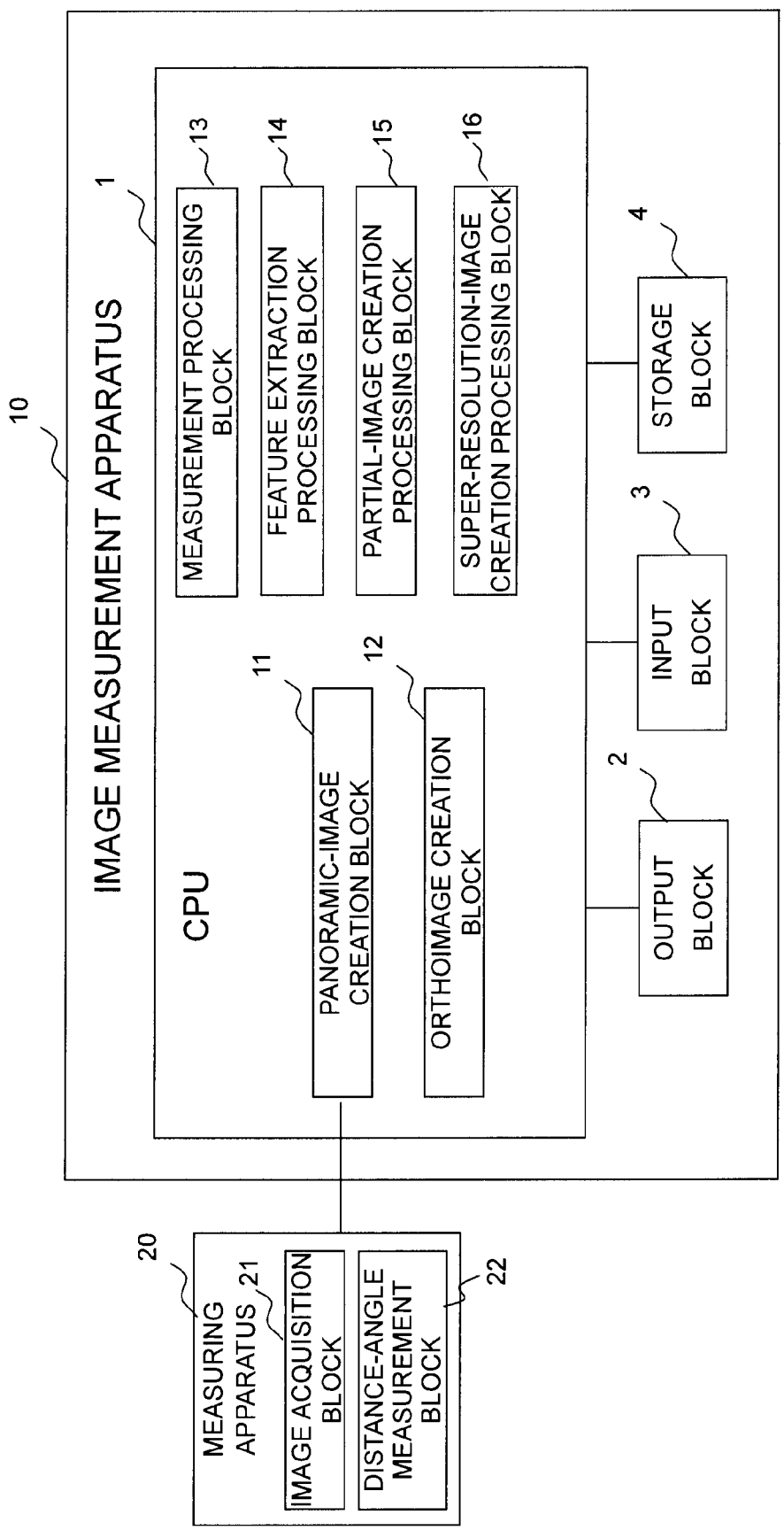
FIG. 14 shows the structure of an image measurement system.

FIG. 14 shows the structure of an image measurement system.

The image measurement system includes a measuring apparatus 20 and an image measurement apparatus 10.

The measuring apparatus 20 includes an image acquisition block 21 for acquiring an image and a distance-angle measurement block 22 for measuring a distance and an angle (or performing three-dimensional measurement). These blocks are motor-driven to acquire an image and to measure the distance and angle. An integral-type apparatus can acquire the image and measure the distance and angle simultaneously.

The image measurement apparatus 10 includes a CPU 1 for performing image measurement processing, an input block 3 for setting appropriate data and inputting an instruction or the like, an output block 2 for outputting an acquired image, and the results of measurement, processing, or the like, and a storage block 4 for writing and reading a set value, input data, output data, intermediate data, and the like at an appropriate timing or as required. The CPU 1 executes comprehensive processing and specialized processing, and includes a panoramic-image creation block 11, an orthoimage creation block 12, a measurement processing block 13, a feature extraction processing block 14, a partial-image creation processing block 15, a super-resolution-image creation processing block 16.

The panoramic-image creation block 11 for creating a panoramic image converts a plurality of image data obtained from the image acquisition block 21 to a panoramic image. The block may also be configured to obtain an image from a panoramic camera.

The orthoimage creation block 12 for creating an orthoimage (orthographic projection image) creates an orthoimage from an obtained image in accordance with distance (three-dimensional) information obtained from the distance-angle measurement block 22. The precision depends on the number of measurement points, and the image can be created when four or more measurement points are provided on the image. As the density increases, more relative-height distortions are corrected, enhancing the precision. When a plurality of images are processed, those images may be combined to a panoramic image. With a higher point density, a more accurate panoramic orthoimage can be created.

The orthoimage will be described later in detail (see 6-1).

The measurement processing block 13 obtains an image by using the image acquisition block 21 of the measuring apparatus 20 and executes processing to measure the distance, angle, and the like by using the distance-angle measurement block 22.

The feature extraction processing block 14 for extracting a feature of an image executes processing to extract features from the images. For example, an edge can be extracted by image processing, and template matching can be performed for a feature point by using a feature thereof as a template.

The partial-image creation processing block 15 performs processing to create a plurality of partial images of a portion near an approximate feature portion extracted by the feature extraction processing block 14.

The super-resolution-image creation processing block 16 obtains a plurality of images by causing the image acquisition block 21 to make very small movements, and performs processing to create a super-resolution image from those images. The micro-movements may be made with high precision by using a motor drive or an image sensor mounted on a piezoelectric element.

FIGS. 6A to 6C show sample structures of the measuring apparatus.

The measuring apparatus 20 for measuring an object to be measured can use different types of structures as listed under (i) to (iv) below, for instance.

(i) All-in-one total station (image total station or image TS, shown in FIG. 6A) where a total station (TS) and a digital camera are combined, or a TS equipped with a digital camera (shown in FIG. 6B) where the camera is mounted on the TS and the camera is aligned with the optical axis of the TS. This type of apparatus is driven by a motor, and the TS and the digital camera move as one body.

(ii) All-in-one laser scanner where a laser scanner and a digital camera are combined or a laser scanner is equipped with a digital camera. This type of apparatus is driven by a motor, and the laser scanner and the camera move as one body (this pattern is the same as that shown in FIGS. 6A and 6B).

(iii) Panoramic camera; a structure for allowing a scanner to read a panoramic image taken by the panoramic camera; a structure for creating a panoramic image from a plurality of images taken by a commercially-available digital camera and reading the image, by means of commercially-available or packaged software; or a structure having a fisheye lens to obtain a panoramic image. Some panoramic cameras achieve a wide field of view optically (360-degree camera: http://www2.sharp.co.jp/docs1/ssc/products/all_direc.html), and some other stationary cameras automatically obtain a panoramic image by turning the camera head. The latter uses an area sensor or a line sensor and can be driven with high precision (http://pencil-jp.net/weblog/archives/01000hardware_for_qtvr_010701line_scan_c cd/). A commercially-available industrial digital camera (CCD camera) or the like may also be driven by a motor (as shown in FIG. 6C).

(iv) Laser scanner. With the single laser scanner, a luminance image and a distance image can be obtained simultaneously. Usually, the quality of the luminance image is much lower than that obtained from a commercially-available digital camera, because the laser scanner is not exclusively intended for that purpose.

The principles of the total station and the laser scanner will be described later in detail (see 6-2).

2. Image Measurement

First Embodiment

A first embodiment of the present invention will be described below.

The structure of the measuring apparatus 20 is (i) or (ii) described above. That is, the measuring apparatus 20 can obtain an image and has a hardware block for measuring the distance and angle.

If the extraction range of the feature extraction processing block 14 is not set as the whole range of the object, a desired extraction range must be specified in preparation for measurement. Before the range is specified, the place to be measured in detail must be determined roughly in a field survey. For observations of long-term changes or the like, the vicinity of the range subjected to feature extraction processing may be marked, or a label may be attached to indicate the position. Then, observations of long-term changes can be automated. Measurement can also be automated by setting a place that has been measured once as a reference coordinate system, so that the position can be measured always. If the whole range is selected first for measurement, efficiency may be enhanced by memorizing a measured position. The whole range may also be measured in each session.

Figure 2:
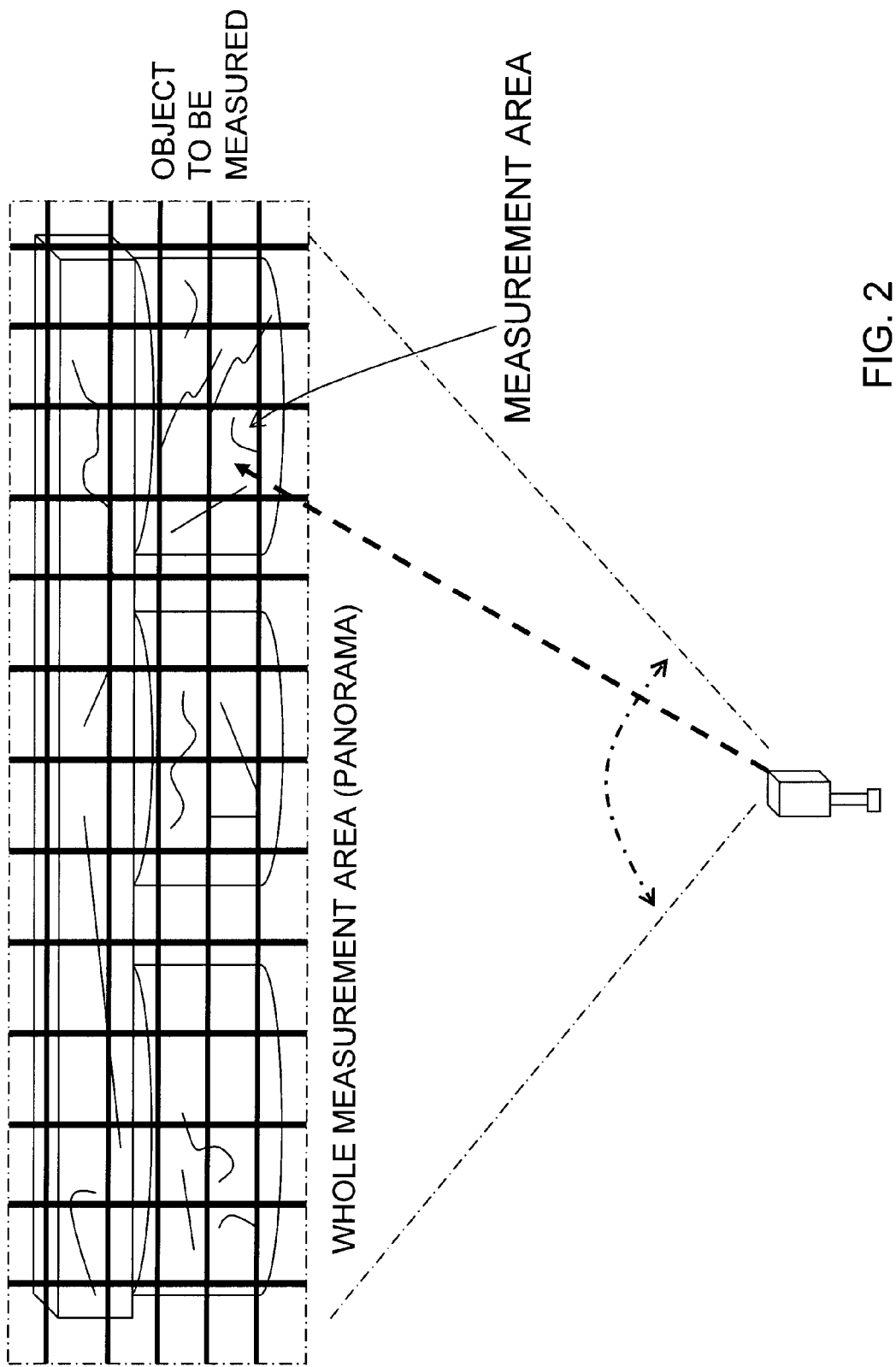
FIG. 2 illustrates the generation of a mesh over the whole range.
Figure 3C:
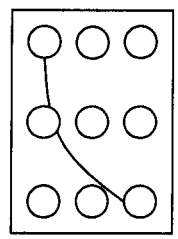
FIGS. 3A to 3C illustrate measurement points in the mesh.
Figure 3B:
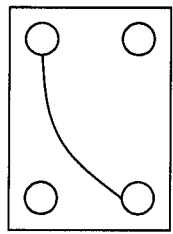
Figure 3A:
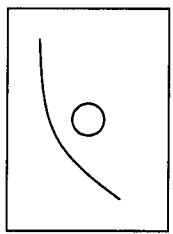
Figure 10:
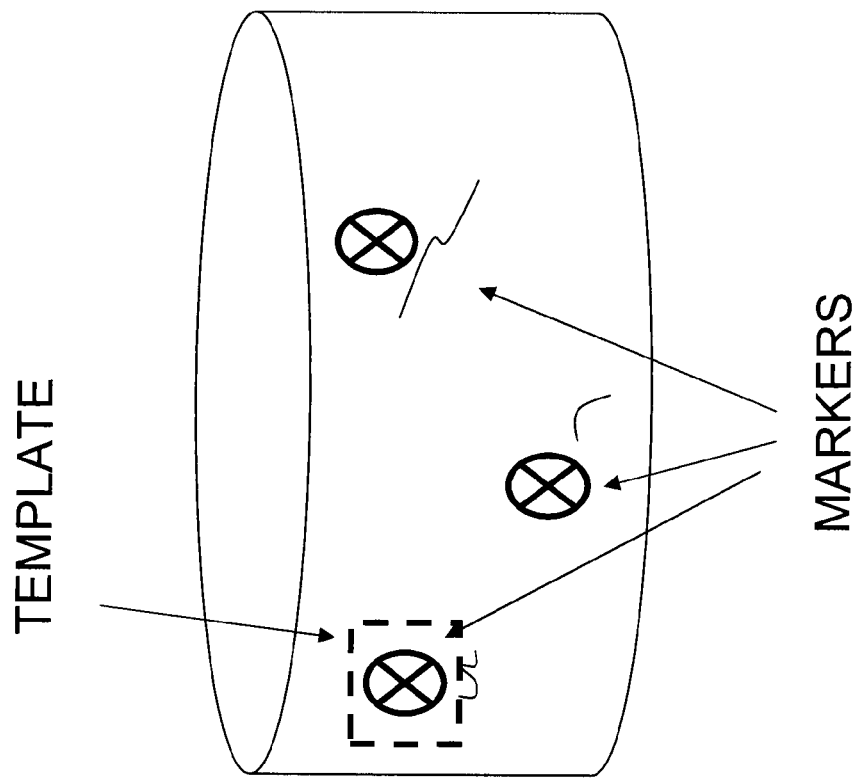
FIG. 10 illustrates template matching using markers.
Figure 15:
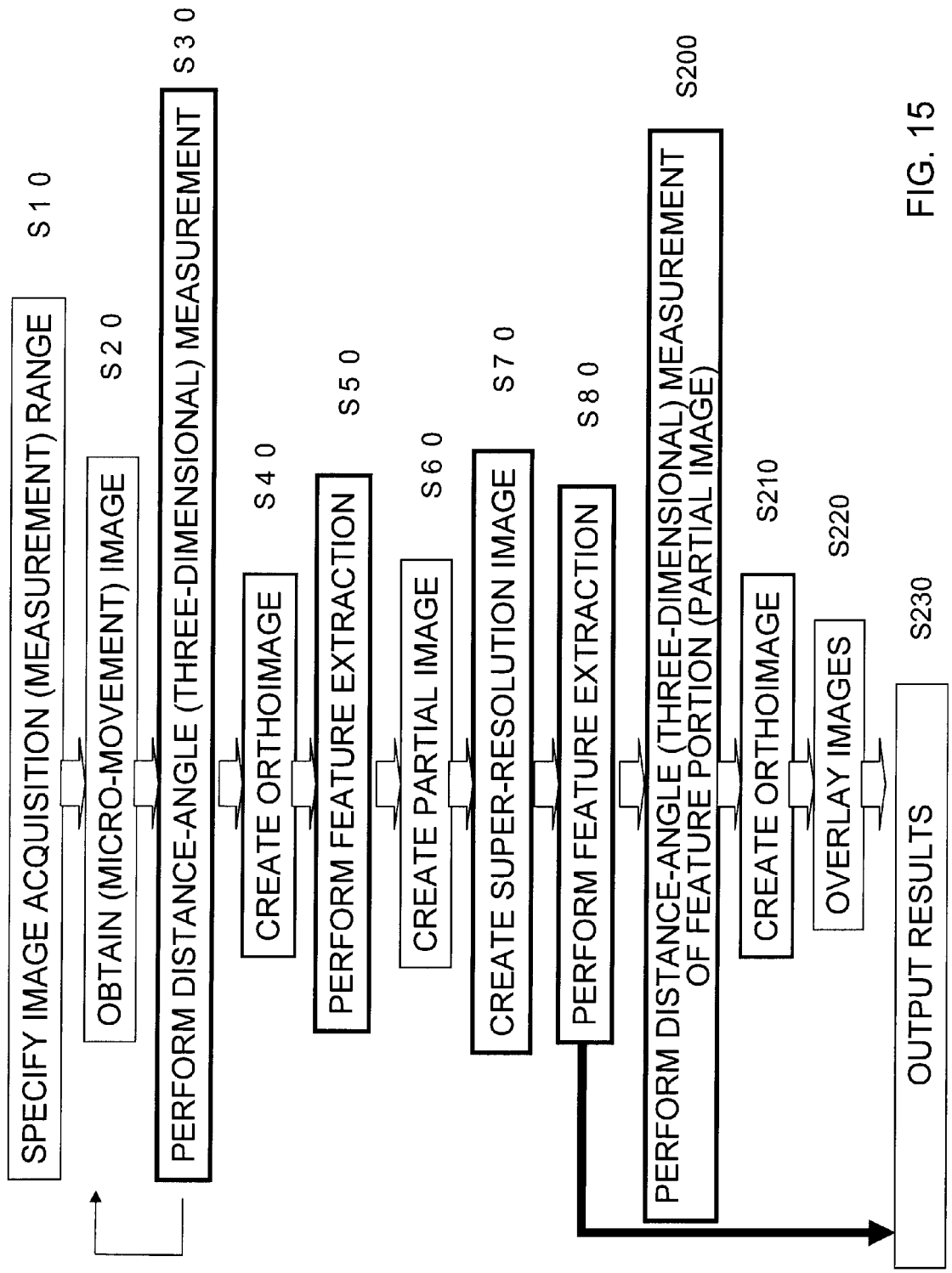
FIG. 15 shows a flowchart of image measurement of a first embodiment (without a high-magnification system).

FIG. 15 shows a flowchart of image measurement of the first embodiment (without a high-magnification system). FIG. 2 illustrates the generation of a mesh over the whole range. FIGS. 3A to 3C illustrate measurement points in the mesh. FIG. 4 illustrates the creation of a panoramic image. FIG. 5 illustrates the creation of partial images. FIG. 10 illustrates template matching using markers.

The steps of processing that uses a single lens magnification, for instance, will be described below.

Step S10

The measurement processing block 13 in the CPU 1 specifies the image acquisition (measurement) range to be measured by the image acquisition block 21 of the measuring apparatus 20. If the whole range is selected as the measurement range, the measurement processing block 13 obtains an image of the whole range. If the whole range does not need to be measured and if observations can be localized, individual images are obtained. For example, if the whole range is specified, the measurement processing block 13 uses the image acquisition block 21 of the measuring apparatus 20 to generate a mesh over the whole range as shown in FIG. 2, to obtain an image from each partition (position), and to scan the whole range.

Step S20

The measurement processing block 13 obtains images in the range while making micro-movements, and the CPU 1 stores those images in the storage block 4. While the image acquisition block 21 is taking the individual images, the measurement processing block 13 performs super-resolution processing for the corresponding area. Therefore, a plurality of images are obtained while micro-movements are being made. If the measurement processing block 13 obtains images in a plurality of positions (a plurality of locations in the mesh, for instance), a plurality of micro-movement images are also obtained in each position. The amount of the micro-movement can be calculated from the horizontal angle and vertical angle of the driven movement, and the lens-to-subject distance. Therefore, the amount is shifted by a desired resolution, for instance. The micro-movements here may not match the pixels of the light receiving device and may differ by one pixel or a few pixels.

Step S30

The measurement processing block 13 uses the distance-angle measurement block 22 of the measuring apparatus 20 to perform distance-angle (three-dimensional) measurement of the image acquisition position, and the CPU 1 stores the measurement result in the storage block 4. This measurement may be conducted on micro-movement images or may be conducted on a central one of those images. The image of each position should have one measurement point in the range or four or more measurement points in its edge as shown in FIGS. 3A, 3B, and 3C, for instance. If a laser scanner is used, which is good at obtaining a dense group of points, the points may be placed at a high density from the beginning, as shown in FIG. 3C. If the whole range is measured, the images should overlap, as shown in FIG. 4, and measurement points of the distance-angle measurement block 22 should be placed in each overlap.

If localized observations or measurement of some important points is performed, without measuring the whole range, the measurement processing block 13 repeats steps S20 and S30 accordingly. If the whole range is required, the measurement processing block 13 repeats steps S20 and S30 until the whole range is covered. Whether to select the whole range can be specified by data or default values stored in the storage block 4 beforehand or from the input block 3 or the like.

Step S40

The orthoimage creation block 12 creates an orthoimage from the obtained image, and the CPU 1 stores the orthoimage in the storage block 4. If the distance-angle measurement block 22 has measured many points, a high-precision orthoimage (orthographic projection image) will be created. With a small number of measurement points, a rough orthoimage will be created.

The orthoimage will be described in detail later, by using an example of an aerial photograph (see 6-1).

Step S50

The CPU 1 reads obtained images from the storage block 4, and the feature extraction processing block 14 extracts features from those images. The features or feature portions can include cracks, fissures, flaws, scratches, marks, and the like.

If the images of a plurality of positions are obtained, feature extraction may be conducted on one representative position or on all images including micro-movement images. In the feature extraction, edge extraction processing is used to measure fissures or cracks, and template matching or other image processing is used to observe long-term changes or the like in a marked position. The processing to be performed can be specified beforehand in the storage block 4 or from the input block 3.

The edge extraction processing will be described later in detail (see 6-3).

The template matching processing or the like is performed to detect a marked area, and a feature position is extracted.

For example, if a marker is attached to indicate the position, this type of image processing is used. If an easily identifiable marker is attached at each position as shown in FIG. 10, this is used as a template in template matching processing.

The search area can be the whole of the obtained image or a partial area. With this processing, a minute feature portion can be found easily.

The template matching will be described later in detail (see 6-4).

Figure 13:
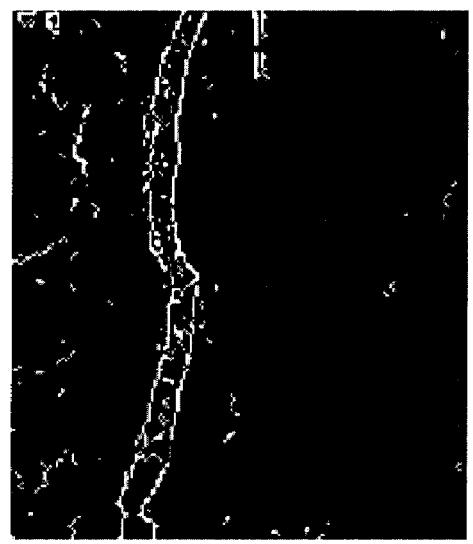
FIG. 13 illustrates edge extraction.

FIG. 13 shows an original image and a result of edge extraction processing using edge extraction operators.

Step S60

The CPU 1 reads an image from the storage block 4, and the partial-image creation processing block 15 creates a partial image thereof at the feature portion extracted by the feature extraction processing block 14 in step S50. FIG. 5 shows an example in which the images obtained in areas subjected to edge extraction processing are grouped, and partial images are created in the group. If the images of the whole range are obtained, each feature-extracted image may be handled as a group, or each image may be broken down into smaller groups.

Step S70

The super-resolution-image creation processing block 16 creates a super-resolution image, and the CPU 1 stores the super-resolution image in the storage block 4.

The super-resolution processing estimates a high-resolution image from a plurality of images or restores an original high-resolution image from a plurality of degraded images. More specifically, the processing is implemented by repeating the alignment (transformation) and combination of the images, for instance.

Figure 16:
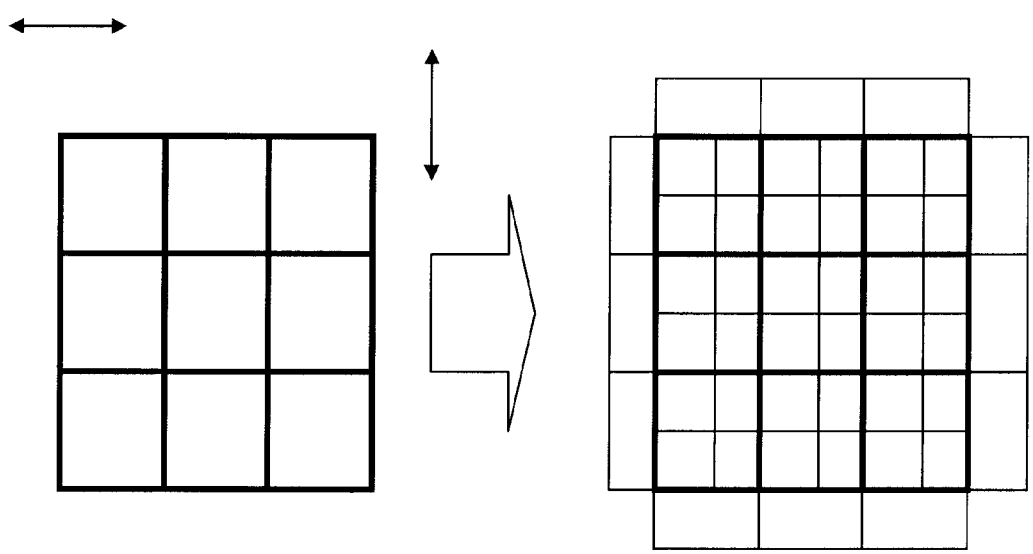
FIG. 16 illustrates the concept of super-resolution processing.

FIG. 16 illustrates the basic concept of the super-resolution processing.

The figure shows an example of an original image and images shifted precisely by a half pixel both up and down, and left and right. While the original image has 3×3=9 pixels, the images shifted by a half pixel quadruple the number of partitions, that is, 6×6=36 cells are made, in the same area. The amount of information is quadrupled just by adding four images of the same area shifted both up and down, and left and right. Theoretically, the number of images required to create a super-resolution image having a resolution of the original image multiplied by n is 2 raised to the power n. To obtain the required images accurately, a mechanism that can shift the images as shown in FIG. 16 by a specified distance, using an image sensor (such as a CCD) precisely driven by a piezoelectric element may be incorporated, and micro-movement images may be obtained from that mechanism.

If the fine-movement mechanism does not shift the images accurately by a specified distance but turns the apparatus (change the angle), the image is transformed, depending on the position it was obtained, because of relative-height distortions and distortions resulting from the inclination when the image was taken. Because the field of view and the point of view of the object and the distance to each measurement position change, both the magnification and the shape change, depending on the position. The images are transformed and distorted in a complicated manner as described above, so that a super-resolution image is created by using the estimation method. More specifically, the extracted images are aligned, transformed to correct (or even out) the distortions, magnified to a desired resolution level, and combined. The combination is repeated a specified number of times or until changes are reduced sufficiently.

The super-resolution processing will be describe later in detail (see 6-5).

Step S80

The CPU 1 reads a super-resolution image created through the super-resolution processing from the storage block 4, and the feature extraction processing block 14 extracts features again from the super-resolution image. The CPU 1 goes to step S230 or S200, as instructed by the storage block 4 or the input block 3.

Since the features are extracted from the super-resolution image, the details of statuses are recorded if the image is printed out. Measurement can also be made on the basis of the result of feature extraction (S200). Then, the CPU 1 may go to step S230 to provide the results of feature extraction directly as the final results or may continue fine measurement, of which procedure will be described below.

Step S200

The measurement processing block 13 uses the distance-angle measurement block 22 of the measuring apparatus 20 to perform distance-angle (three-dimensional) measurement of the extracted feature portion along the feature portion or in the entire area of the partial image, and the CPU 1 stores the result of measurement in the storage block 4. The measurement can be made in the entire area of the created partial image as shown in FIG. 5 or in the extracted feature portion. For example, with this processing, the dimensions in the X and Y directions of a crack and a difference in level in the direction of depth can be accurately obtained. Alternatively, unevenness around the crack can also be observed.

Step S210

The orthoimage creation block 12 of the CPU 1 creates a detailed orthoimage of the part in accordance with the measured points and images. This orthoimage can be used as a detailed crack drawing.

Step S220

If there are a plurality of measurement positions and if the whole range is selected, the CPU 1 overlays the detailed images on the entire orthoimage created in step S40 (or replaces the entire image with the detailed images). Because the coordinates are known, the images can be aligned easily. Now, a crack distribution map of the whole object to be measured and its detailed drawings can be created.

Step S230

The CPU 1 stores the results in the storage block 4, outputs the results to the output block 2, or performs both the storage and the output. The results include the overall drawing, the detailed drawings, and the information of irregularities therein, so that a cross sectional view can be created and the unevenness and size of the crack can be determined along the crack.

3. Second Embodiment of the Image Measurement Apparatus

A second embodiment of the present invention will now be described.

Features are extracted with higher precision by obtaining images under low magnification and high magnification and performing the super resolution processing. In the second embodiment, a low magnification system can also create a panoramic image (orthoimage).

Figure 17:
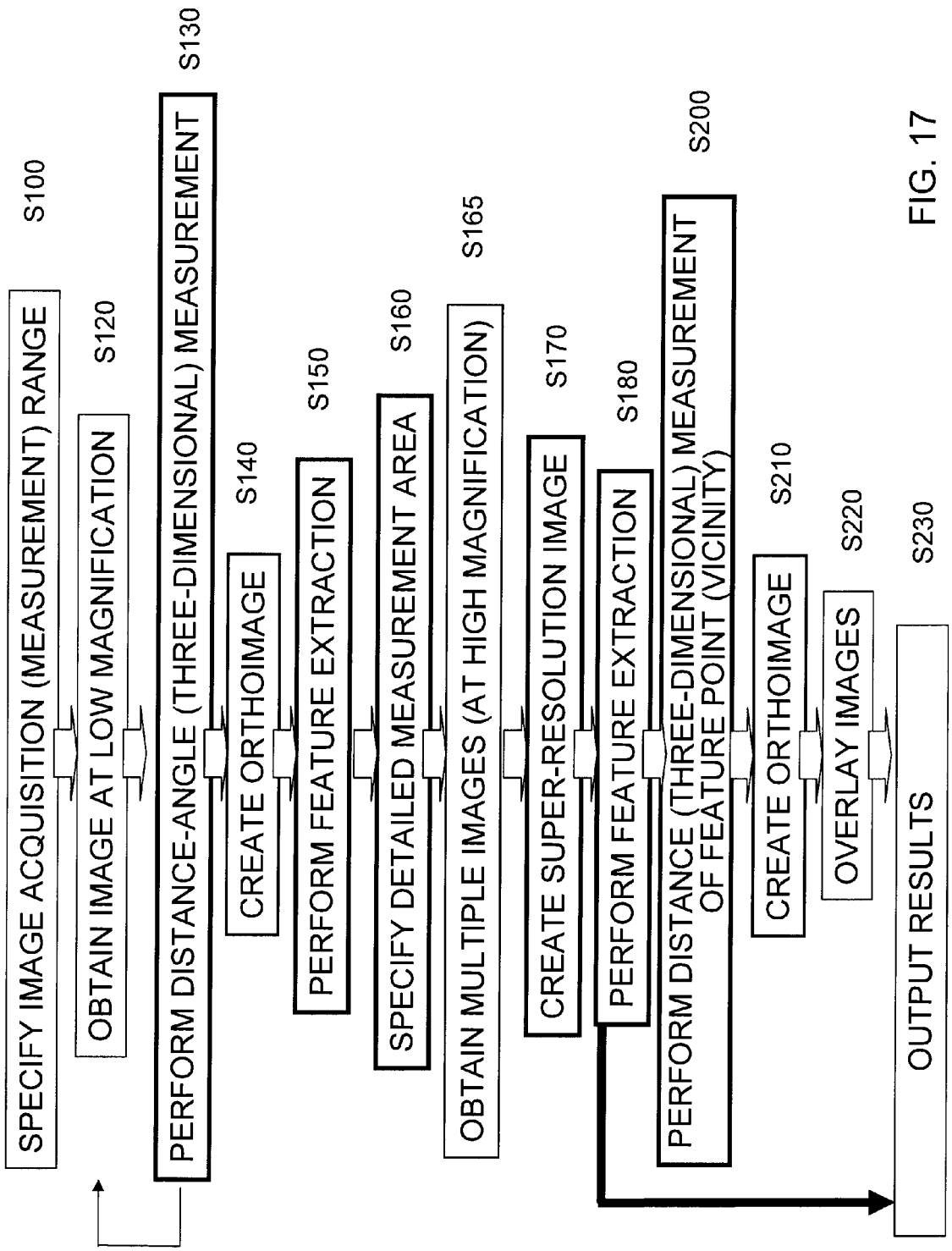
FIG. 17 shows a flowchart of image measurement of a second embodiment (high magnification system and low magnification system).

FIG. 17 shows a flowchart of image measurement of the second embodiment (high magnification system and low magnification system). FIG. 2 illustrates the generation of a mesh over the whole range.

The individual steps of the processing will be described below:

Step S100

The measurement processing block 13 in the CPU 1 specifies the image acquisition (measurement) range to be measured by the image acquisition block 21 of the measuring apparatus 20. If the whole range is selected as the measurement range, the measurement processing block 13 obtains the image of the whole range. If the whole range does not need to be measured and if observations can be localized, individual images are obtained.

For example, if the whole range is specified, the measurement processing block 13 uses the image acquisition block 21 of the measuring apparatus 20 to generate a mesh over the whole range as shown in FIG. 2 to obtain an image from each position, and to scan the whole range.

Step S120

The measurement processing block 13 uses the image acquisition block 21 to obtain an image under low magnification, and the CPU 1 stores the image in the storage block 4. The micro-movement images are not obtained. Accordingly, if images of the whole range are obtained, with a mesh generated as shown in FIG. 2, for instance, a single image is taken from each mesh partition.

Step S130

The measurement processing block 13 uses the distance-angle measurement block 22 of the measuring apparatus 20 to perform distance-angle (three-dimensional) measurement of the image acquisition position, and the CPU 1 stores the measurement result of measurement in the storage block 4. Each image should have one measurement point in the range or four or more measurement points in its edge, as shown in FIGS. 3A and 3B. If the whole range is measured, the images should overlap, as shown in FIG. 4, and measurement points of the distance-angle measurement block 22 should be placed in the overlap.

If localized observations or measurement of some important points is performed, without measuring the whole range, steps S120 and S130 are repeated accordingly. If the whole range is required, steps S120 and S130 are repeated until the whole range is covered. Whether to select the whole range can be specified by data and default values stored in the storage block 4 beforehand or from the input block 3 or the like.

Step S140

The orthoimage creation block 12 creates an orthoimage from the obtained image, and the CPU 1 stores the orthoimage in the storage block 4. If the images of a plurality of ranges have been obtained with overlaps and if the distance-angle measurement block 22 has performed measurement, the orthoimage created here becomes a panoramic image. The panoramic image has high precision because the image reflects the three-dimensional coordinate values.

Step S150

The feature extraction processing block 14 in the CPU 1 extracts features from the obtained images. The feature extraction method is as described earlier.

Step S160

The measurement processing block 13 in the CPU 1 specifies a measurement area for a portion extracted as a feature. The measurement processing block 13 creates a partial image of the feature-extracted area and specifies an imaging area of the high magnification system.

Step S165

The measurement processing block 13 uses the image acquisition block 21 of the measuring apparatus 20 to obtain an image under high magnification from each measurement area, and the CPU 1 stores the image in the storage block 4. The measurement processing block 13 uses the image acquisition block 21 to obtain images while making micro-movements.

Step S170

The super-resolution-image creation processing block 16 creates a super-resolution image of each feature extraction portion, and the CPU 1 stores the super-resolution image in the storage block 4.

Step S180

The CPU 1 reads the super-resolution image created through the super-resolution processing from the storage block 4, and the feature extraction processing block 14 extracts features again from the super-resolution image.

The CPU 1 goes to step S230 or S200, as instructed by the storage block 4 or the input block 3.

Since the features are extracted from the super-resolution image, the details of statuses are recorded if the image is printed out. The distance and angle can be measured from the extracted feature portion (S230). Then, the CPU 1 may go to step S230 to provide the results of feature extraction directly as the final results or may continue fine measurement, of which procedure will be described below.

Steps S200 to S230 of the subsequent processing are the same as those in the first embodiment, described with reference to FIG. 15.

A commercially-available digital camera or the like can be used in place of steps S100 and S120 described above. In that case, the digital camera should take an image of the position to be measured. The CPU 1 lets the (image measurement) apparatus read the image and stores the image in the storage block 4.

Then, the CPU 1 aligns the apparatus with the taken image through steps S130 and S140 to create an orthoimage. Because the distance-angle measurement has been performed, the CPU 1 can obtain the dimensions and scale from the taken image.

4. Third Embodiment of Image Measurement

A third embodiment of the present invention will be described next.

In the third embodiment, the measuring apparatus 20 having any of structures described earlier under (i) to (iv) can be used. The measuring apparatus 20 having the type (iii) structure is a panoramic camera that can take an image automatically with the camera portion driven both up and down, and left and right by a motor, or a commercially-available industrial camera that can be driven both up and down, and left and right by a motor (FIG. 6C).

In the third embodiment, images are taken simply while micro-movements are being made; features are extracted to provide the feature points as partial images; and the super-resolution processing is performed to extract fine feature portions.

Figure 18:
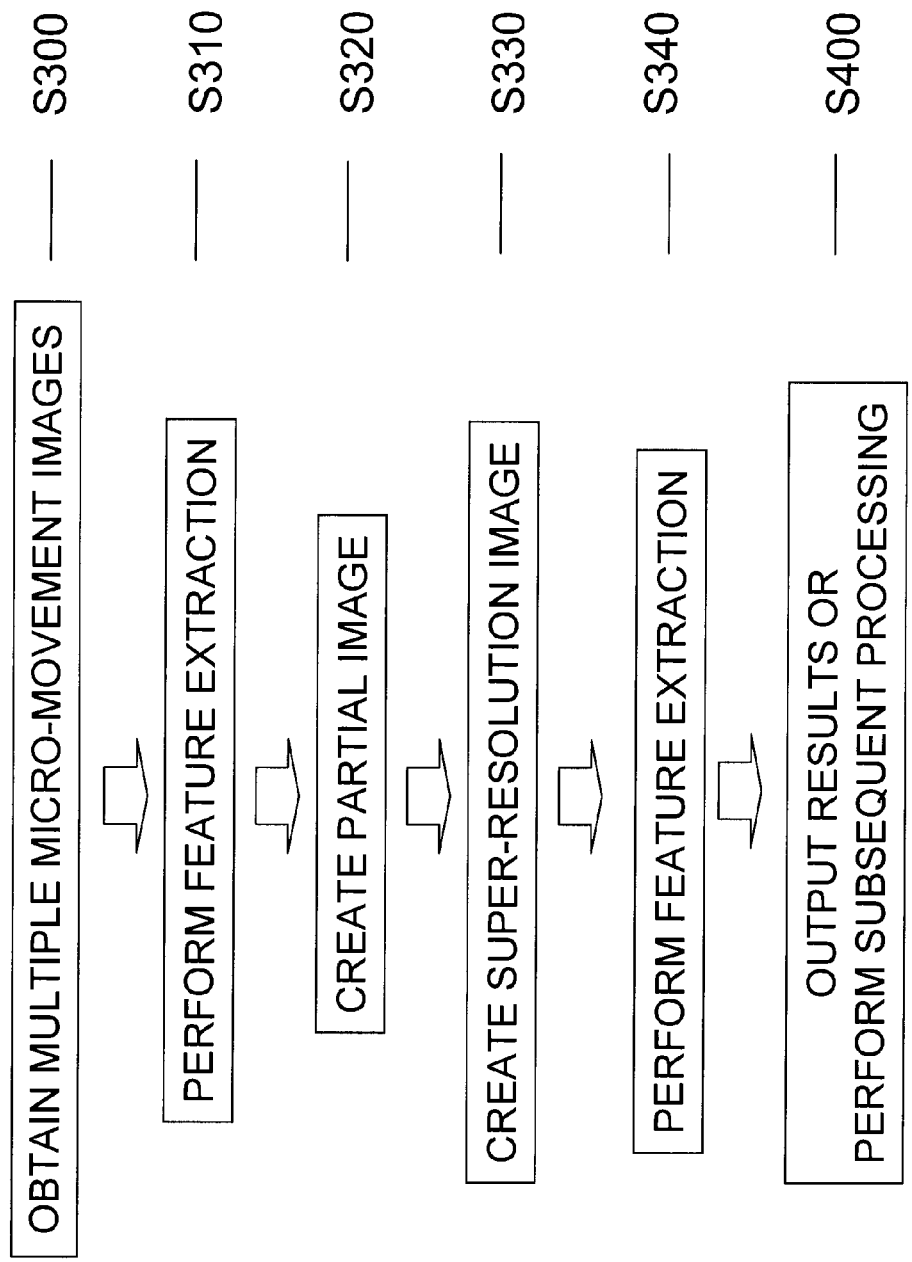
FIG. 18 shows a flowchart of image measurement of a third embodiment.

FIG. 18 shows a flowchart of image measurement of the third embodiment. FIG. 2 illustrates the generation of a mesh over the whole range, and FIG. 5 illustrates the creation of partial images.

The steps of the processing will be described below.

Step S300

The measurement processing block 13 uses the image acquisition block 21 of the measuring apparatus 20 to obtain the image to be measured, and the CPU 1 stores the image in the storage block 4. If the whole range is selected as the measurement range, the measurement processing block 13 obtains an image of the whole range. If the whole range does not need to be measured and if observations can be localized, individual images are obtained. For example, if the whole range is specified, the measurement processing block 13 uses the image acquisition block 21 of the measuring apparatus 20 to generate a mesh over the whole range as shown in FIG. 2, to obtain an image from each position, and to scan the whole range. While the individual images are being obtained, the measurement processing block 13 performs the super resolution processing of the corresponding areas, so that a plurality of images are obtained while micro-movements are made in each area.

Step S310

The CPU 1 reads a plurality of obtained images from the storage block 4, and the feature extraction processing block 14 extracts features from the images. In the feature extraction, edge extraction processing is used to measure fissures or cracks, and template matching or other image processing is used to observe long-term changes or the like in a marked position. In the edge extraction processing, anything can be used: line detection operators or Canny operators may be used; and a Laplacian-of-Gaussian filter (LoG filter) may be used to obtain a zero-crossing point.

Step S320

The partial-image creation processing block 15 creates a partial image of the extracted feature portion, and the CPU 1 stores the image in the storage block 4. With the example shown in FIG. 5, the areas subjected to edge extraction processing are grouped, and a plurality of partial images of those parts are created.

Step S330

The super-resolution-image creation processing block 16 creates a super-resolution image, and the CPU 1 stores the image in the storage block 4.

Step S340

The feature extraction processing block 14 in the CPU 1 extracts a feature again from the super-resolution image.

Step S400

The CPU 1 outputs results or goes to subsequent steps S200 to S230, as instructed by the storage block 4 or the input block 3.

Since the feature is extracted from the super-resolution image, the details of statuses are recorded if the image is printed out.

The processing of steps S200 to S230 is the same as in the first and second embodiments, described with reference to FIGS. 15 and 17.

The distance-angle measurement block 22 can be configured as a stereo camera (this will be described later).

5. Modified Embodiments

Other embodiments of the present invention will be described next. Those embodiments can be applied to the first to third embodiments described earlier.

5-1. First Modified Embodiment

Using a Panoramic Image Created by an External Apparatus

This embodiment simplifies the specification of the image acquisition (measurement) range. An overall image is obtained in advance, and automatic measurement is performed by inputting the image to the image measurement apparatus 10.

Figure 19:
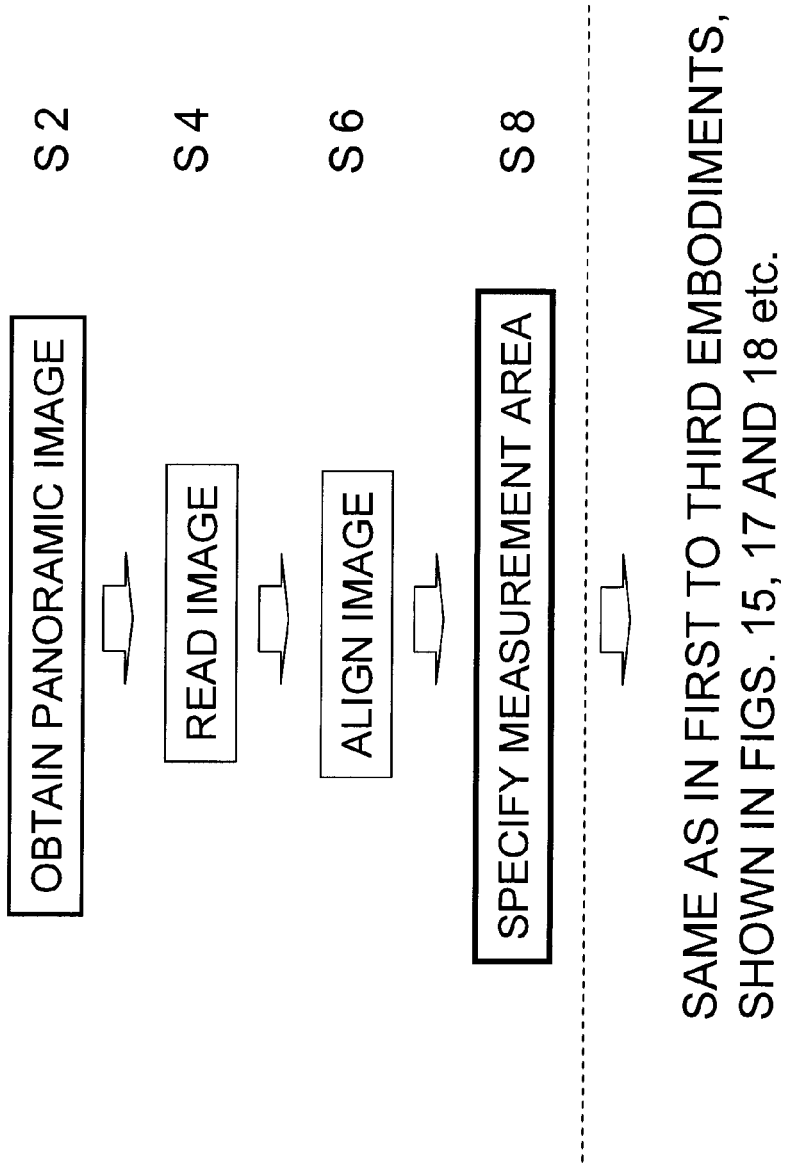
FIG. 19 shows a flowchart of processing using a panoramic image in preliminary processing.

FIG. 19 shows a flowchart of processing using a panoramic image in preliminary processing.

The steps will be described below.

Step S2: Obtaining a Panoramic Image

To cover the whole range to be measured, a plurality of images are created with an overlap by an image acquisition apparatus such as a commercially-available digital camera. A panoramic image is created by a panoramic image synthesis program. This program may be supplied with the digital camera or may be separately sold. If a fisheye lens is used with the digital camera, a wide range can be captured into a single image, but the resolution may not be very high. The panoramic image differs from the orthoimage, which will be described later, in that the three-dimensional coordinates are not reflected and that the precision of the image is comparatively low.

A panoramic camera may also be used. One type of panoramic camera obtains a panoramic image by scanning a CCD with precision, and another type obtains a wide-angle image at a time by using an optical concave mirror. The output of the panoramic camera is a panoramic image. The precision scanning type of panoramic camera is reliable in terms of precision.

Step S4

The CPU 1 reads the obtained image into the storage block 4 of the measurement apparatus by using the input block 3, an interface, or the like.

Step S6

The CPU 1 aligns the measuring apparatus 20 with the taken image.

In this step, the CPU 1 displays the read image on the screen of the output block 2 of the image measurement apparatus 10. While viewing the image, the operator specifies, for example, at least four points from both the right end and the left end of the image by using the input block 3. The measurement processing block 13 of the CPU 1 lets the distance-angle measurement block 22 perform measurement in accordance with the specification. Now, the image measurement apparatus 10 can be aligned with the panoramic image. More accurate alignment can be made with a greater number of specified points.

Then, the CPU 1 goes to step S10 to specify the measurement area with the measurement processing block 13. The area may be specified manually or determined in accordance with features extracted by the feature extraction processing block 14. The subsequent steps are the same as in the first to third embodiments (FIGS. 15, 17, 18).

With the rough overall image input by obtaining the panoramic image beforehand, automatic measurement can be conducted in a narrow measurement range. Because the measurement range can be narrowed first, automation is much facilitated.

5-2. Second Modified Embodiment

The Distance-Angle Measurement Block 22 Uses a Stereo Image

In this embodiment, the distance-angle (three-dimensional coordinate) measurement block 22 measures three-dimensional coordinates from a stereo image. In comparison with the TS or a laser scanner, high-precision, high-definition (high-density) three-dimensional coordinates can be obtained because stereo matching processing is conducted on a super-resolution image.

In this embodiment, the measuring apparatus 20 having any of the structures (i) to (iv) described earlier can be used. The camera is driven both up and down, and left and right by a motor. Since more than tens of thousands of three-dimensional coordinates (points) can be obtained basically from the right and left stereo images, this structure is suitable for the panoramic camera or the image TS. A high-precision camera block allows high-precision measurement. If a small number of three dimensional coordinates are obtained, the image TS can efficiently create a panoramic image or obtain an orthoimage from a first image by calculating three dimensional coordinates from the distance-angle measurement block 22 and obtaining detailed three-dimensional coordinates from the right and left images of a feature extracted by the feature extraction processing block 14.

Figure 7:
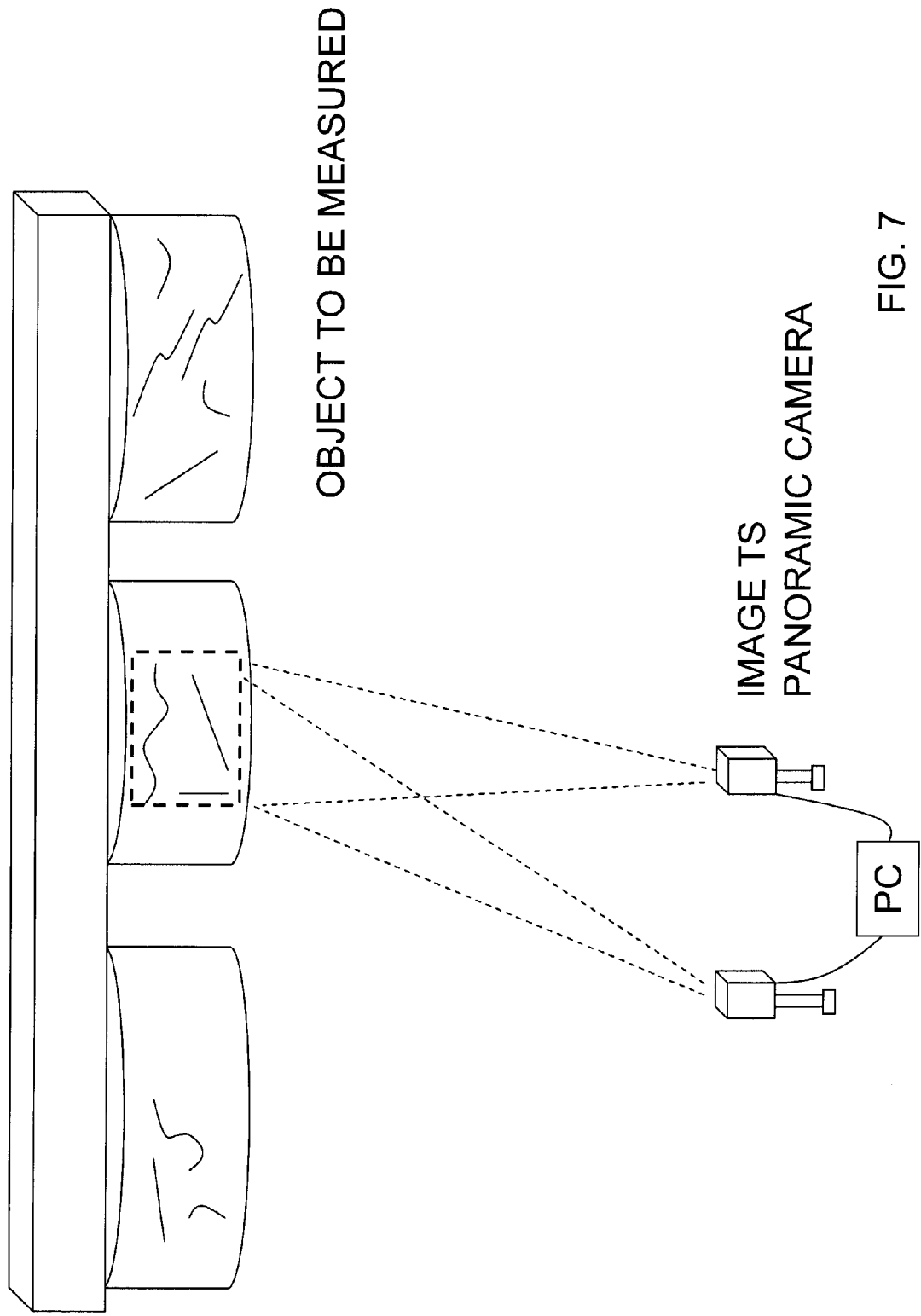
FIG. 7 illustrates stereo image acquisition by using a panoramic camera.

FIG. 7 illustrates stereo image acquisition by using a panoramic camera.

As shown in FIG. 7, two measuring apparatuses are placed to obtain an image in stereo. The right and left images are taken for the same area at the same time with the two apparatuses connected by a PC.

The flowchart of image measurement is the same as in the first or second embodiment, shown in FIG. 15 or 17, except for the distance-angle measurements (three-dimensional measurements) in step S30 or S130, and in step S200. In step S30 or S130, the measurement processing block 13 in the CPU 1 uses the measuring apparatus 20 to obtain the three-dimensional coordinates by obtaining a point (FIGS. 3A and 3B) to be measured in three dimensions from right and left images (images obtained from the right and left apparatuses shown in FIG. 7) through template matching.

With the measuring apparatus 20 having the (i) type structure, if a TS function is provided, the measurement processing block 13 uses the distance-angle measurement block 22 to perform measurement of a point shown in FIG. 3A or 3B, and the results are converted to three-dimensional coordinates and used as the reference coordinates. Then, in the orthoimage creation processing in step S40 or S140, the CPU 1 performs stereo matching of the right and left images, and the orthoimage creation block 12 creates an orthoimage by using the three-dimensional coordinates of the obtained plane and the reference coordinates. The created orthoimage has high precision.

The CPU 1 performs steps S200 and S210 in the same way as step S30 or S130, and step S40 or S140, that is, performs stereo matching of right and left images of a partial image of a feature portion extracted from a super-resolution image, so that a precision orthoimage of the feature portion and the whole of the partial image can be obtained.

With this structure, three-dimensional measurement of a feature-extracted portion can be performed with precision.

5-3. Third Modified Embodiment

Using a Scanner to Take a Luminance Image by an Internal Sensor of the Scanner Simultaneously with Distance Information In this embodiment, super-resolution processing is performed with a luminance image that can be obtained in laser scanning by a sensor in a laser scanner simultaneously with distance information.

Figure 9:
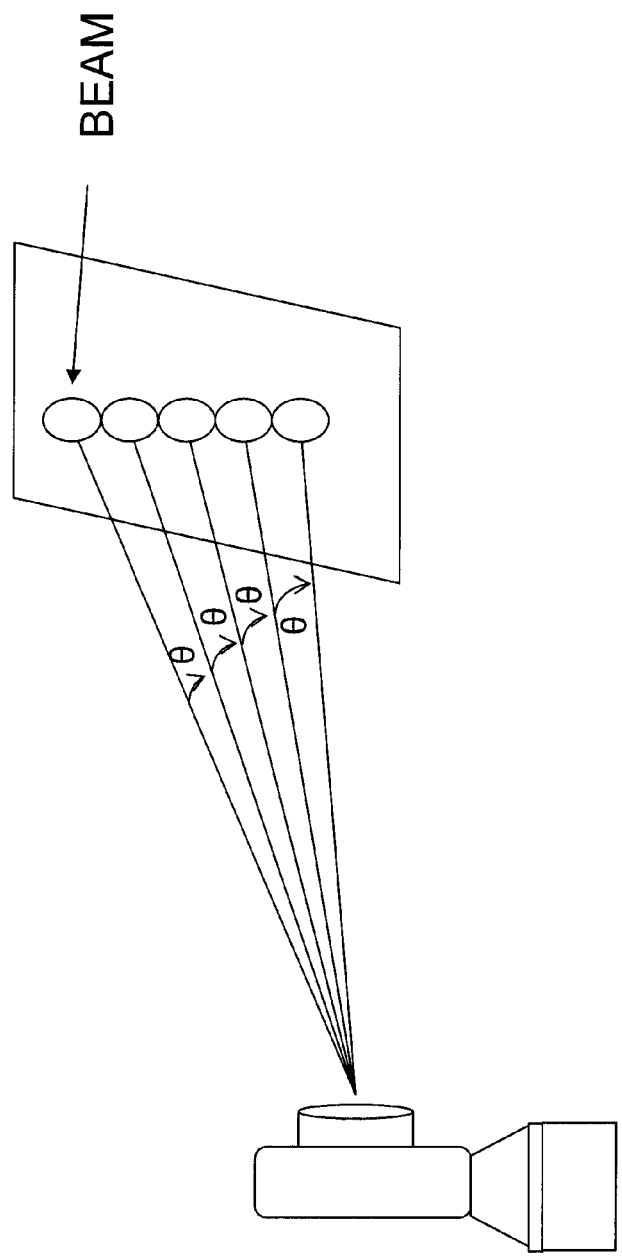
FIG. 9 illustrates a laser beam.

FIG. 9 illustrates laser beams.

The laser scanner measures the distance of each point on an object while it is scanning the object, and can obtain a large amount of distance information in a short period. Because the measuring apparatus 20 obtains angle information when it obtains the distance, the three-dimensional coordinates of the object, centering around the scanner, can be obtained. The scanner originally obtains the distance information alone. Some scanners, however, can form an image based on the intensity of laser light returning from each point (http://www.krcnet.co.jp/technical/3Dlaser/3Dlaser02.htm). Some other scanners are structured to obtain a luminance value by an internal luminance sensor at the same time as when the distance information of each point is obtained and to form an image accordingly.

Since the laser scanner is not originally intended for the acquisition of an image (or cannot be optimized because of restrictions on the structure of the apparatus), the image quality is relatively low, and the diameter of the beam increases as the distance increases, because of its principle (see FIG. 9).

If the laser scanner receives light by a light receiving device having a single light receiving plane, it is important to provide super resolution by handling distance information obtained from each point as color information in an image, by handling intensity information as an image, or by handling stored luminance information as an image. This can be applied to all the embodiments of the present invention. If the laser scanner receives reflected light by a light receiving block such as a CCD, an image obtained by the light receiving block is handled directly as image data (such as a first image and a second image).

When the flowchart shown in FIG. 15 is used (a single optical image acquisition system), the image acquisition in step S20 and the distance-angle (three-dimensional) measurement in step S30 can be performed simultaneously. In the orthoimage creation processing in steps S40 and S210, the obtained point information needs to be just arranged as an image.

The flowchart shown in FIG. 17 is used with a laser scanner including two optical measurement systems, one with low magnification and the other with high magnification. In this case, steps S120 and S130 can be performed at the same time. In the orthoimage creation processing in steps S140 and S210, the obtained point information needs to be just arranged as an image.

5-4. Fourth Modified Embodiment

Using a Panoramic Camera of the Third Embodiment

Figure 27:
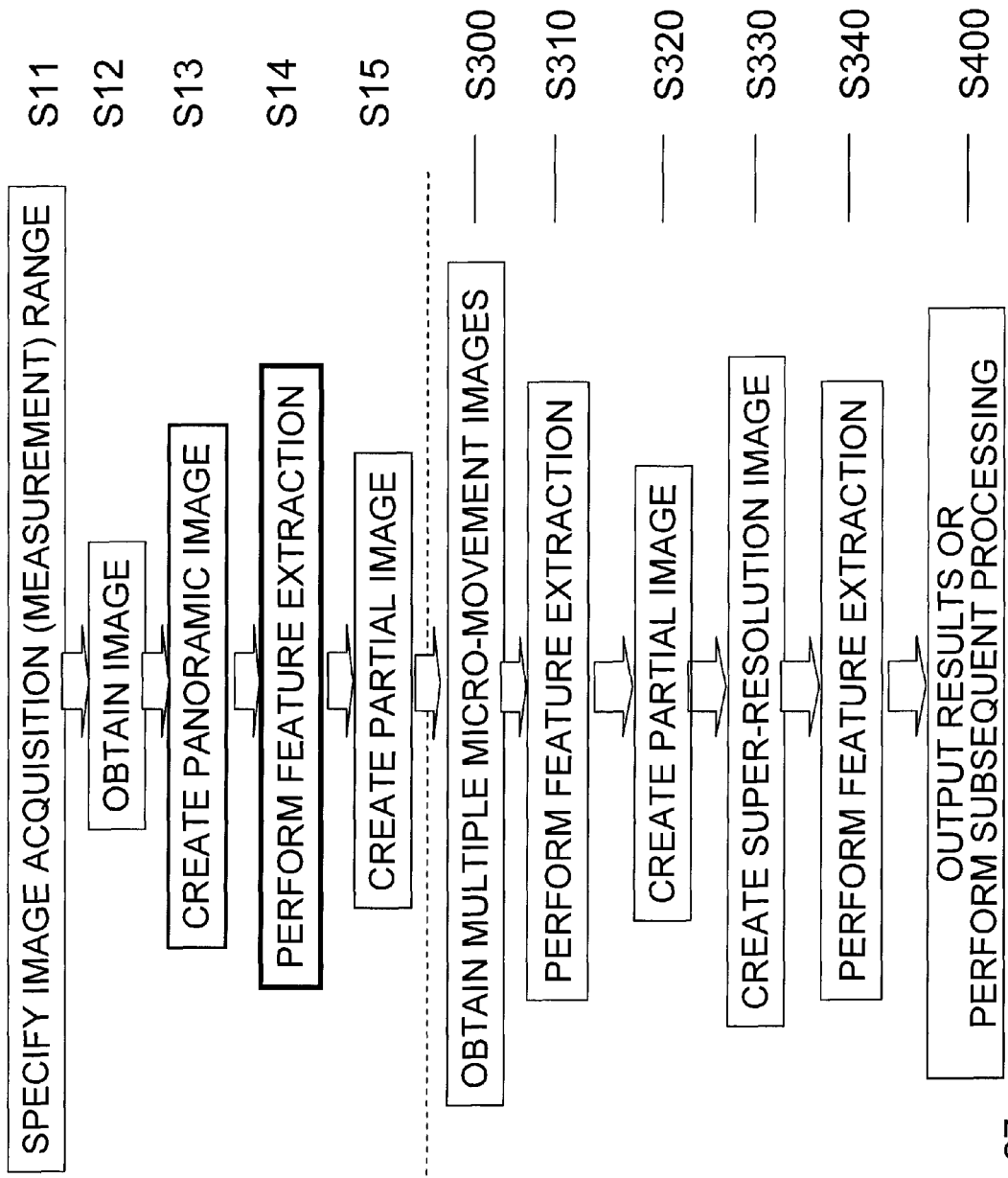
FIG. 27 shows a flowchart of processing using a panoramic camera.

FIG. 27 shows a flowchart of processing using a panoramic camera.

In this embodiment, the panoramic camera is used as the measuring apparatus 20. The steps of the processing will be described below.

Step S11

The measurement processing block 13 in the CPU 1 specifies the image acquisition (measurement) range to be measured by the image acquisition block 21 of the measuring apparatus 20. If the whole range is selected as the measurement range, the measurement processing block 13 obtains an image of the whole range. If the whole range does not need to be measured and if observations can be localized, individual images are obtained. For example, if the whole range is specified, the measurement processing block 13 uses the image acquisition block 21 of the measuring apparatus 20 to generate a mesh over the whole range, to obtain an image from each partition (position), and to scan the whole range.

Step S12

The measurement processing block 13 obtains images in the range while making micro-movements, and the CPU 1 stores the images in the storage block 4. When the image acquisition block 21 is taking the individual images, the measurement processing block 13 performs super resolution processing for the corresponding area. Therefore, a plurality of images is obtained while micro-movements are being made. Accordingly, if the measurement processing block 13 obtains images at a plurality of positions (different positions in a mesh partition), a plurality of images are obtained with micro-movements in each position.

Step S13

The measurement processing block 13 creates a panoramic image, and the CPU 1 stores the result in the storage block 4.

Step S14

The CPU 1 reads the panoramic image from the storage block 4, and the feature extraction processing block 14 extracts features from the image.

Step S15

The CPU 1 reads the image from the storage block 4, and the partial-image creation processing block 15 creates a partial image of each feature portion extracted in step S14 by the feature extraction processing block 14.

Steps S300 to S400 of the subsequent processing are the same as in the third embodiment.

6. Processing

Processing will be described below in detail.

6-1. Orthoimage (Orthographic Projection Image)

Figure 20:
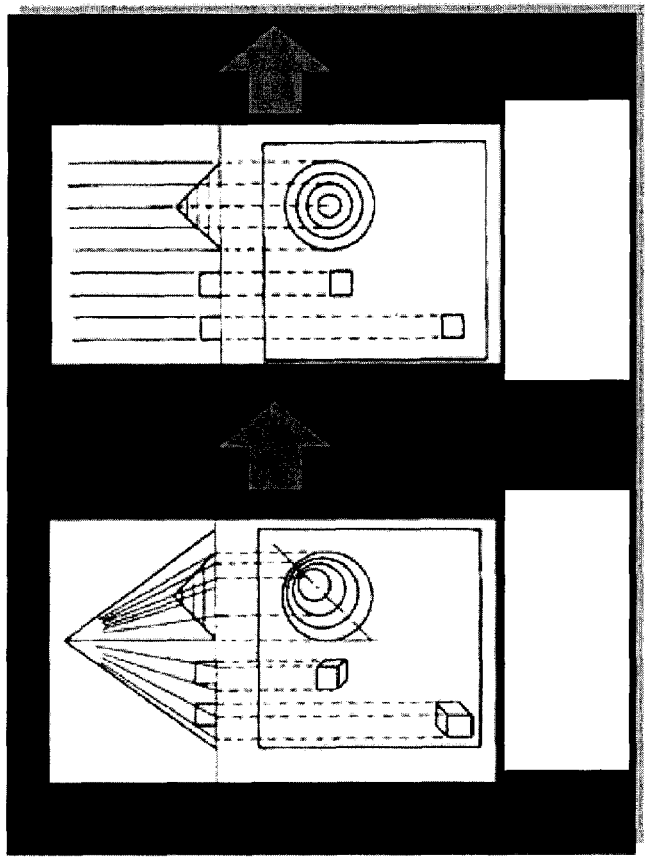
FIG. 20 illustrates an orthoimage (orthographic projection image).

FIG. 20 illustrates an orthoimage (orthographic projection image).

Figure 21:
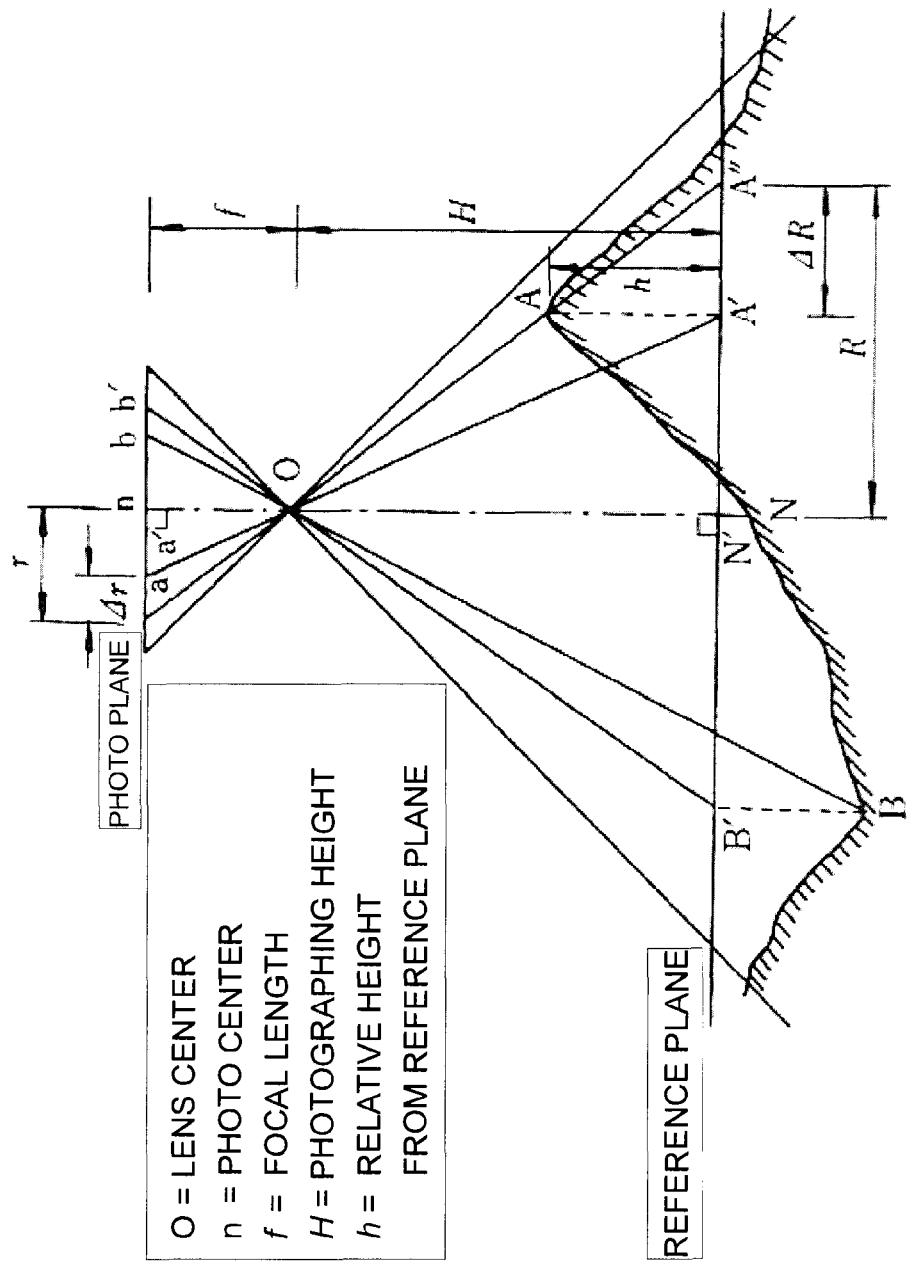
FIG. 21 illustrates the deflection of an image depending on the relative height in perspective projection.

FIG. 21 illustrates the deflection of an image, depending on relative heights in perspective projection.

The orthoimage (orthographic projection image) is a parallel projection image as in a map, created from a perspective projection image. The image is modified by correcting relative-height distortions in accordance with the three-dimensional coordinates. With a higher density of three-dimensional coordinates, the orthoimage can be obtained with higher precision.

Relative-height distortions include the following:

Deflection of a photographed image from the photograph center point, caused by the unevenness (relative height) of the subject (surface of the ground, in the shown example)

Variations in photographing scale, occurring in the same photograph, caused by differences in distance (H) between the lens and the subject (surface of the ground)

An aerial photograph is obtained through a perspective projection system, centering around the lens. If the relative height of the surface of the ground varies, the image deflects radially around the point (N=plumb point) where light passing the lens meets the surface of the ground perpendicularly. As shown in FIG. 21, point A is projected through point O to point a. Projected point A' of point A on the reference plane should be projected to a' but is actually projected with a deflection of a'a. In other words, the amount of deflection of the image caused by the relative height (h) is increased an amount equal to the distance A'A'' on the reference plane multiplied by the scaling factor. Assume that O denotes the lens, and H denotes the height from the reference plane (photographing height), then the amount of deflection of point A is obtained as follows:

$$\Delta r = A'A'' \cdot f/H$$

Therefore, if the three-dimensional coordinates of the subject are known, the amount of deflection $\Delta r$ can be corrected in accordance with the principle of perspective projection.

6-2. Principles of Total Station and Laser Scanner

An ordinary total station used in surveying can be used in distance-angle measurement. The total station is a combination of a theodolite having a function to measure an angle horizontally and vertically with high precision and an electro-optical rangefinder for measuring the distance of the subject by light or laser. In recent years, a total station incorporating an image sensor or a total station that can be driven by a motor have been developed.

A laser scanner is similar to the total station in its principle. The laser scanner applies a laser beam to each point on the subject, scans the surface with the laser beam, and obtains distance information on the surface as a slope distance depending on the reflection time from the point. The laser scanner can measure automatically a great number of points (several thousands to several millions of points) at a high density at a time. The scanning speed is high, but the precision is lower than that of the total station.

Because these apparatuses can obtain distance information and the parallel and horizontal angles simultaneously, three-dimensional coordinates can be calculated. Although the TS performs triangulation, the two apparatuses are similar if the mechanical position of the TS itself is specified as the reference.

Figure 8:
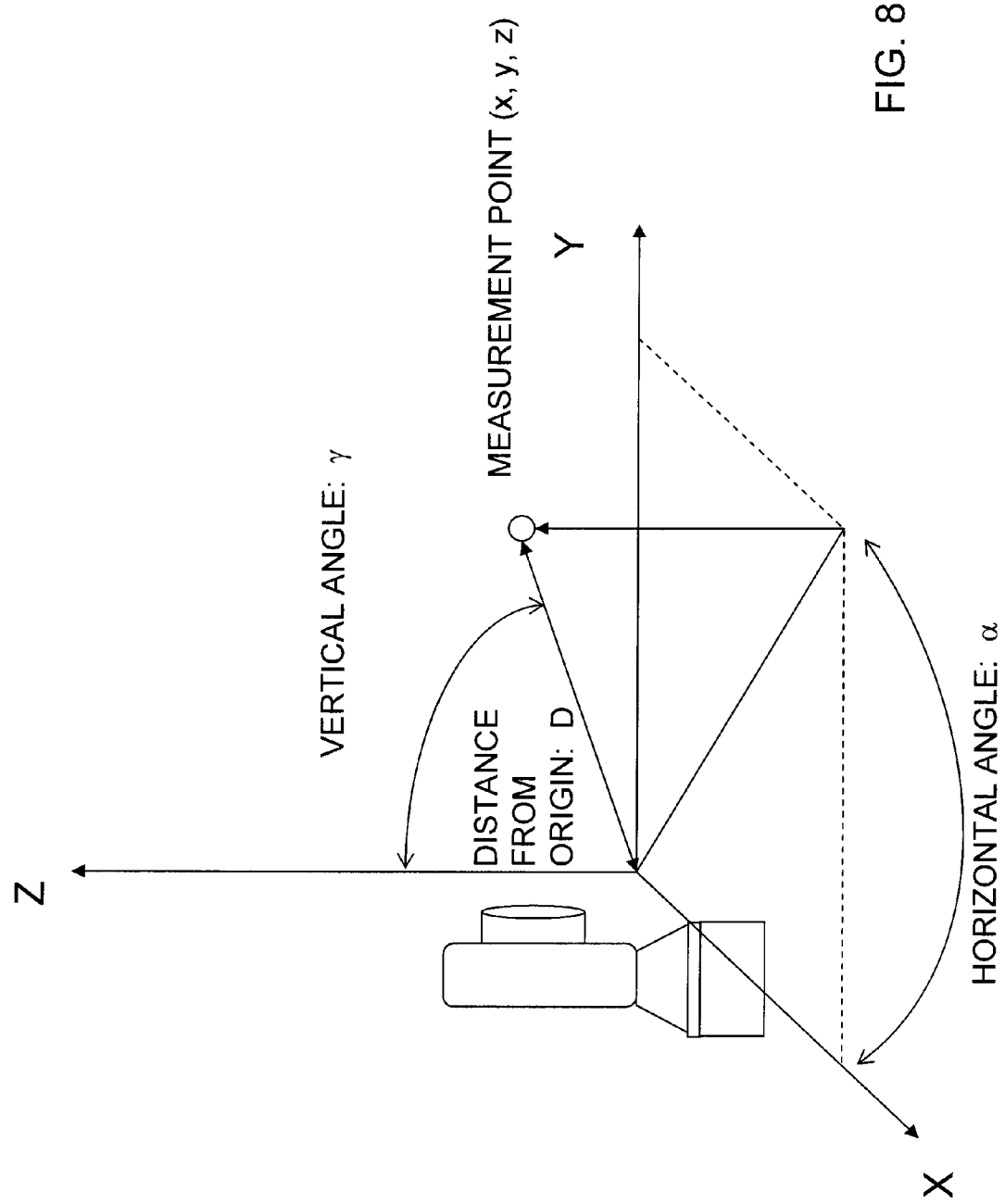
FIG. 8 illustrates a coordinate system.

FIG. 8 illustrates the principles of the total station and the laser scanner.

The three-dimensional coordinates p(x, y, z) of the subject are:

$$p(x,y,z) = (D \cdot \sin \gamma \cdot \sin \alpha, D \cdot \sin \gamma \cdot \cos \alpha, D \cdot \cos \gamma)$$

where $\alpha$ is the horizontal angle, $\gamma$ is the vertical angle, and D is the distance from the origin.

The coordinates are transformed to the terrestrial coordinate system by using four or more reference points. If a local reference point is allowed, the reference point can be specified in a desired place, and measurement is made by the TS. GPS can also be used.

6-3. Edge Detection Processing

In the edge extraction processing, anything can be used: Line detection operators may be used; a Laplacian-of-Gaussian filter (LoG filter) may be used to obtain a zero-crossing point; or Canny operators may be used (J. F. Canny, "A computational approach to edge detection," IEEE Transaction on Pattern Analysis and Machine Intelligence, 8(6): 679-698, November 1986). An example of obtaining a zero-crossing point with a LoG filter will be described below.

Figure 22:
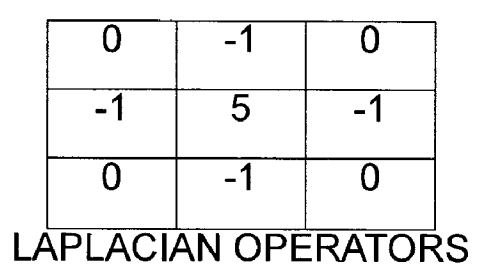

FIG. 22 illustrates Laplacian operators.

FIG. 23 illustrates line detection operators.

(1) Edge Extraction by Log Filter

In edge extraction processing, the image is sharpened, and a zero-crossing point of the gray-scale value of the image is extracted as an edge.

The image is blurred first by using a Laplacian filter, a LoG filter, or the like. By subtracting the blurred image from the original image, a sharpened image can be obtained.

The LoG filter smoothes pixels in a local region by using a Gaussian distribution function and applies Laplacian operators. In comparison with methods using the other differential operators, this method has higher noise immunity and can extract an edge from a relatively smooth variation in gray scale value, by obtaining a zero-crossing point from filter output. This is because the LoG filter is applied to a comparatively wide range by smoothing while the other differential filters are applied to a local range (see "Image Analysis Handbook," edited by Mikio Takagi and Akihisa Shimoda, University of Tokyo Press, 1991).

$$g(i,j) = f(i,j) - \nabla^2 f(i,j)$$

$g(i, j)$: Sharpened image $f(i, j)$: Input image $\nabla^2 f(i, j)$: Laplacian input image As for $\nabla^2 f(i, j)$, differential operators of different forms are possible.

FIG. 22 shows example differential operators but the operators which can be used are not limited to these examples.

Gaussian operators may also be used.

Thus, a sharpened image is obtained. The sharpened image can be obtained by many other methods.

Arithmetic processing expressed by the equation given below can be used instead of the digital method described above.

The equation expresses an arithmetic operation using Gaussian operators.

$$\nabla^2 G(x, y) = \frac{x^2 + y^2 - 2\sigma^2}{2\pi\sigma^6} \cdot \exp(-(x^2+y^2)/2\sigma^2)$$

where σ is a parameter of a Gaussian function.

In that case, the difference is expressed as follows.

$$g(x,y)=f(x,y)-\nabla^2 G(x,y)$$

g(x, y): Sharpened image
f(x, y): Input image
$\nabla^2 G(x, y)$: Laplacian of Gaussian input image The same effect can be obtained by taking a tight-focused image (corresponding to f(x, y)) and an out-of-focus image (corresponding to $\nabla^2 G(x, y)$) of the same subject and obtaining a difference image of the two.

An edge is extracted from the sharpened image.

In the edge extraction processing, an edge is extracted as a zero-crossing point of the gray-scale value of the sharpened image obtained here.

Just zero-crossing points are imaged. Alternatively, an edge image is formed by displaying positive areas and negative areas divided by the zero-crossing points in white and black, respectively.

The edge image can be overlaid on the original image or the sharpened image, to display an edge-enhanced image.

(2) Other Operators

A specific direction or a specific shape can also be emphasized and extracted.

For example, FIG. 23 shows line detection operators used to detect a vertical line. A horizontal line can be detected by using operators including +1 placed in a row and by convoluting them in the image. A desired shape can be detected by forming a correlational filter for that shape to be extracted, more specifically, by forming a matrix by placing +1 along the shape to be detected and −½ or −1 in other positions.

6-4. Template Matching

Template matching can use the normalized correlation method, the sequential similarity detection algorithm (SSDA), and the like. In the above embodiments, any of those methods can be used. If the sequential similarity detection algorithm is used, the processing speed is enhanced.

(1) Sequential Similarity Detection Algorithm

Figure 24:
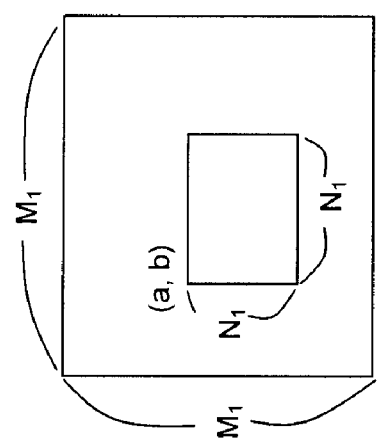
FIG. 24 illustrates an input image and a template image.

FIG. 24 illustrates an input image and a template image.

A template image of $N_1$ by $N_1$ pixels is moved on a search range $(M_1-N_1+1)^2$ in an input image of $M_1$ by $M_1$ pixels, which is greater than the template image, as shown in the figure. Searching is assumed to be finished when the top left position of the template image is obtained such that R(a, b) in the equation given below is minimized.

The sequential similarity detection algorithm can be expressed by the following equation.

A point where the residual error R(a, b) is minimized is the position of the image to be obtained. The processing speed is enhanced by stopping the addition when the value of R(a, b) exceeds the previous minimum value of the residual error and moving to the next (a, b).

$$R(a,b) = \sum_{m_1=0}^{N_1-1} \sum_{n_1=0}^{N_1-1} |I_{(a,b)}(m_1, n_1) - T(m_1, n_1)|$$

$T(m_1, n_1)$: Template image
$I_{(a,b)}(m_1, n_1)$: Partial image of the target image
(a, b): Top left position of the template image
R(a, b): Residual error (2) Normalized Correlation Method A template image of $N_1$ by $N_1$ pixels is moved on a search area of $(M_1-N_1+1)^2$ in an input image of $M_1$ by $M_1$ pixels, which is greater than the template image, as shown in the figure. Searching is assumed to be finished when the top left position of the template image is obtained such that C(a, b) in the equation given below is maximized.

The normalized correlation method can be expressed by the following equation.

$$C(a,b) = \sum_{m_1=0}^{N_1-1} \sum_{n_1=0}^{N_1-1} \frac{\{I_{(a,b)}(m_1,n_1)-\bar{I}\}\{T(m_1,n_1)-\bar{T}\}}{\sqrt{I_{\sigma_{ab}} T_\sigma}}$$

where $$\bar{I} = \frac{1}{N_1^2} \sum_{m_1=0}^{N_1-1} \sum_{n_1=0}^{N_1-1} I_{(a,b)}(m_1, n_1)$$

$$\bar{T} = \frac{1}{N_1^2} \sum_{m_1=0}^{N_1-1} \sum_{n_1=0}^{N_1-1} T(m_1, n_1)$$

$$I_{\sigma_{ab}} = \frac{1}{N_1^2} \sum_{m_1=0}^{N_1-1} \sum_{n_1=0}^{N_1-1} \{I_{(a,b)}(m_1, n_1) - \bar{I}\}^2$$

$$T_\sigma = \frac{1}{N_1^2} \sum_{m_1=0}^{N_1-1} \sum_{n_1=0}^{N_1-1} \{T(m_1, n_1) - \bar{T}\}^2$$

$I_{(a,b)}(m_1, n_1)$: Partial image of the input image
$T(m_1, n_1)$: Template image 6-5. Super-Resolution Processing FIG. 25 shows an example of super-resolution image actually created.

If an approximate amount of a micro-movement is known in advance and if a great number of images are taken with micro-movements at different positions, the result of estimation becomes more accurate. In the above embodiments, an image can be created with a desired resolution by calculating a necessary resolving power on the basis of the relationship between the apparatus-to-subject distance and the image area on the image sensor (magnification) and the pixel resolution and by specifying the number of images and the amount of micro-movement. If the distance information can be obtained from the TS or laser scanner and if the image can be obtained simultaneously, the calculation can be made on the apparatus.

For example, if the distance of the subject is 30 meters, if the telescope has a magnification of 30×, and if a resolution of 0.3 mm is specified on a pixel of the sensor, 0.2 mm can be obtained by specifying a double or quadruple super resolution and specifying 4 to 16 micro-movement positions.

The micro-movements are driven by a motor. Alternatively, the image sensor may be vibrated by a piezoelectric element.

With vibrations made by the piezoelectric element, the precision of image synthesis processing can be enhanced easily and reliably.

Figure 26:
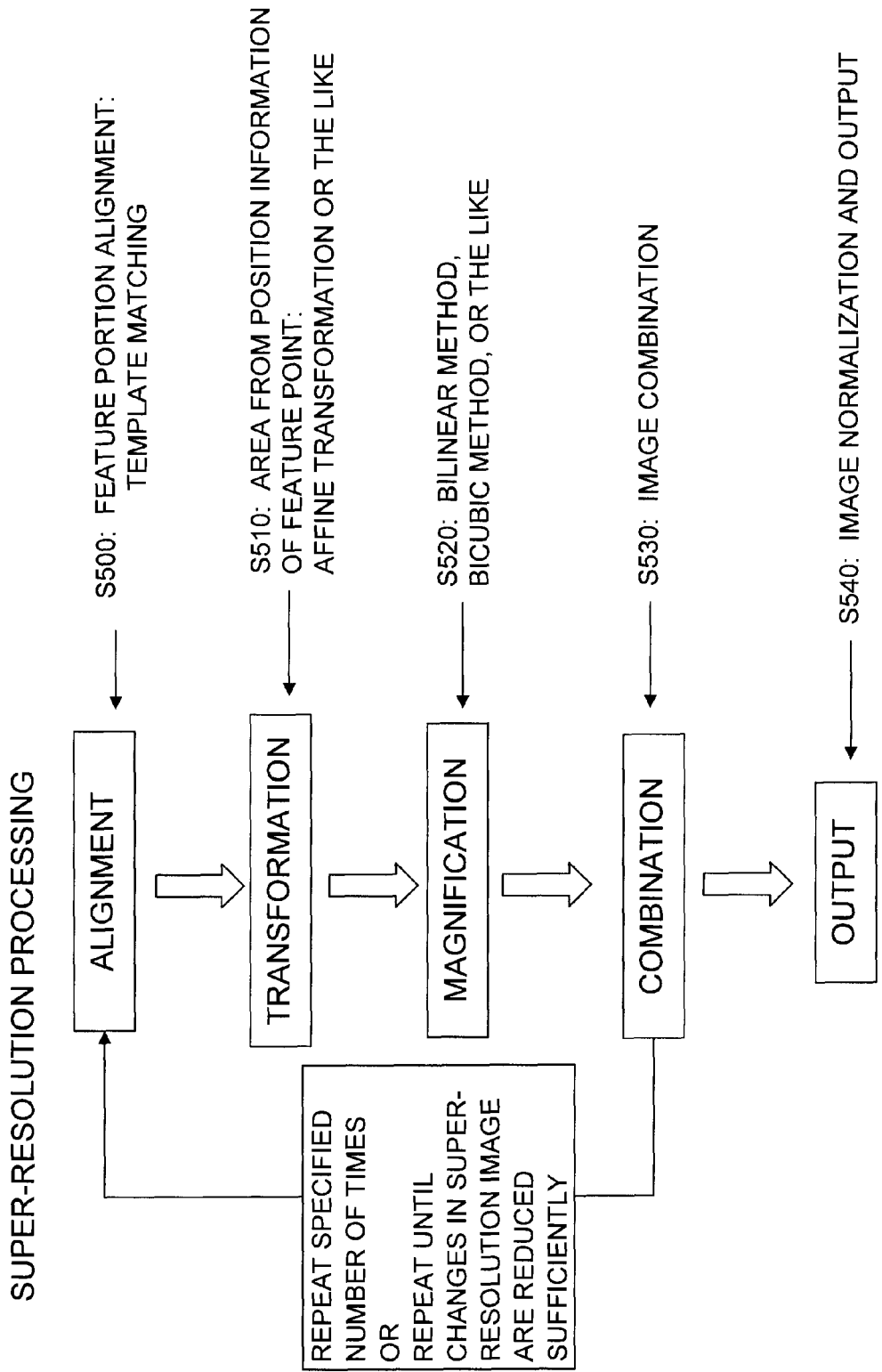
FIG. 26 shows a flowchart of super resolution processing.

FIG. 26 shows a flowchart of super resolution processing.

FIGS. 11A to 11C illustrate templates and search areas.

Figure 12C:
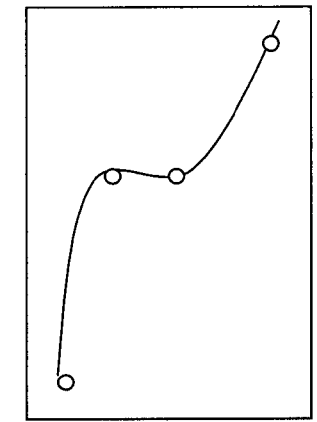
FIGS. 12A to 12C illustrate feature points.
Figure 12B:
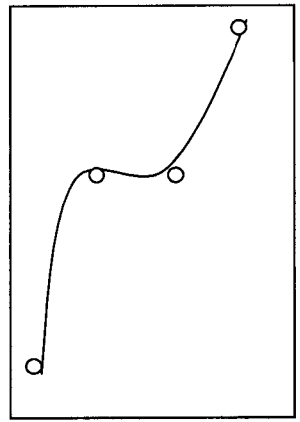
Figure 12A:
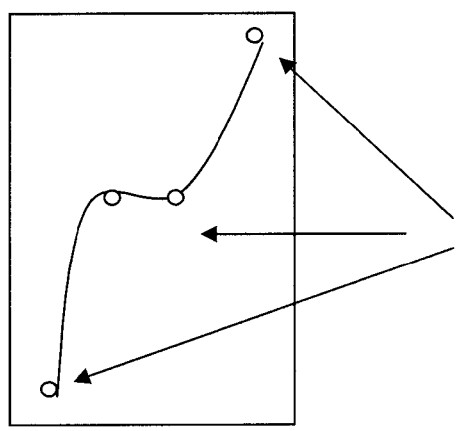

FIGS. 12A to 12C illustrate feature points.

The steps of the processing will be described below.

Step S500

The super-resolution-image creation processing block 16 of the CPU 1 aligns partial images created from the position information of the feature-extracted image.

With the partial images created from a plurality of images taken while micro-movements are being made, an approximate amount of difference on each of the partial images can be calculated from information on the micro-movement. For example, the amount can be calculated from the distance to the measurement position when the image was obtained, that is, distance information from the feature extraction processing block 14 or partial-image creation block and the corresponding angle information (see the equations given in the description of the TS and the laser scanner). Accordingly, the amount of difference is calculated from the equation, and the amount becomes the amount of alignment. An approximate position may be calculated from the distance information of a representative position, instead of the accurate distance to the position of the partial image.

More accurate positioning can be performed by the processing described later, even without the distance information. If position information is available, the search area can be narrowed, so that the processing speed is enhanced.

The super-resolution-image creation processing block 16 performs template matching between extracted partial images. In the processing, the super-resolution-image creation processing block 16 uses a feature portion extracted from a reference image (central image before a micro-movement is made, for instance) as a template and compares the template with feature portions at the same position of other micro-movement images. For example, the whole of the cut-out area (partial image) shown in FIG. 11A can be used as a template in a search. Alternatively, template matching can be performed with a part of an extracted feature. FIG. 11A shows an example of using a part of a partial image of one of multiple images as a template. FIGS. 11B and 11C show an example of specifying a search area in another image and performing template matching in the area. The search area can be narrowed by approximating the amount of difference according to the equation, because the position would not differ greatly.

The template matching processing is the same as the one described earlier. The image to be compared with can be a gray-scale image or a two-valued image after edge extraction.

Step S510

The super-resolution-image creation processing block 16 then transforms the image. For example, the central image of the plurality of pre-micro-movement images is used as the reference, and their partial images and the reference are used. A projective transformation, an affine transformation, and other operations are used (if the sensor is vibrated by a piezoelectric element, the transformation is not needed, just a translation needs to be performed).

For example, points that have already been measured (the positions of the points have already been known), as shown in FIGS. 3B and 3C, are used. Four or more inflection points (on a crack, in the shown example) extracted by the feature extraction processing block 14 are detected as feature points in a plurality of images, as shown in FIGS. 12A to 12C, and image transformation is performed.

The super-resolution-image creation processing block 16 substitutes image coordinates into the observation equation given below to obtain affine coefficients and transforms each image.

Equations of affine transformation $$u_{i+1} = a_1 u_i + a_2 v_i + a_3$$

$$v_{i+1} = a_4 u_i + a_5 v_i + a_6 \quad (1)$$

Here:

$a_1 a_6$: affine parameter, (u, v): image coordinate at frame i

The basic image coordinates (before micro-movement) and the post-micro-movement image coordinates are assigned to the equations given above to formulate an observation equation; the affine coefficients $a_1$ to $a_6$ are obtained; and the post-micro-movement image is transformed to have the same form as the pre-micro-movement image.

Step S520

The super-resolution-image creation processing block 16 magnifies the image. For example, if the image is doubled, a double image area should be prepared; and if the image is quadrupled, a quadruple image area should be prepared. This processing uses the linear (bilinear) interpolation method, the third-order interpolation (cubic) method, or the like.

Step S530

The super-resolution-image creation processing block 16 combines the images. Just addition is performed. The plurality of images are added. If the amount of the micro-movement is known in advance and if the number of micro-movement images is determined from the resolving power, the super-resolution-image creation processing block 16 repeats the processing for the individual micro-movement images. In other cases, such as when a large number of micro-movement images have been obtained, the super-resolution-image creation processing block 16 repeats the processing until changes in the images are reduced sufficiently. That is, the super-resolution-image creation processing block 16 repeats the processing until changes in the combined image are reduced sufficiently. For example, a threshold level is specified, and the amount of change is calculated by subtracting the immediately preceding combined image from a newly combined image.

Step S540

The super-resolution-image creation processing block 16 stores the image in the storage block 4 and outputs the image to the output block 2, and the processing ends.

The present invention can be applied to image measurement at a variety of constructions such as buildings and smokestacks, in addition to bridges.

The present invention can be applied to measure a variety of shapes of flaws, marks, fissures, and the like, in addition to cracks.

The present invention can be applied to measure the shapes of cracks and the like under the surface by using X-rays and the like, in addition to laser light or visible light.

This application claims priority from Japanese Patent Application 2007-222002, filed Aug. 29, 2007, which is incorporated herein by reference in its entirety.

What is claimed is:

1. An image measurement apparatus comprising:
  a measurement processing block for obtaining a plurality of first images of an object to be measured, taken while micro-movements, which do not match pixels and shift, are being made in an imaging area;
  a feature extraction processing block for extracting an approximate feature portion of the object from the plurality of first images obtained by the measurement processing block;
  a partial-image creation processing block for creating a plurality of first partial images by grouping the plurality of first images obtained by the measurement processing block in the vicinity of the approximate feature portion extracted by the feature extraction processing block; and a super-resolution-image creation processing block for creating a super-resolution image from the plurality of first partial images created by the partial-image creation processing block;

a distance-angle measurement block for measuring the distance to and the angle of a point contained in the first image;

an orthoimage creation block for creating an orthoimage from individual points in the first image, in accordance with the distance measured by the distance-angle measurement block and the position of the first image;

wherein the feature extraction processing block extracts a detailed feature portion from the super-resolution image, and the super-resolution-image creation processing block aligns the plurality of first partial images taken while the micro-movements are being made in the imaging area, in accordance with the approximate feature portion, and combines the images to form a super-resolution image containing the detailed feature portion, thereby the super-resolution-image creation processing block estimates a high-resolution image from a plurality of images or restores an original high-resolution image from a plurality of degraded images and magnifies the image.

2. An image measurement apparatus according to claim 1, further comprising a panoramic-image creation block for creating a panoramic image of the whole by combining the plurality of first images taken under the low magnification, wherein the feature extraction processing block extracts an approximate feature portion of the object from the panoramic image.

3. An image measurement apparatus according to claim 1, wherein the distance-angle measurement block contains at least one of a laser scanner, an electro-optical rangefinder, and a total station to measure the distance and angle.

4. An image measurement apparatus according to claim 1, wherein the first image is created in an overlapping manner as a plurality of stereo images of the object to be measured, taken from different imaging positions, and the distance is obtained from the stereo images.

5. An image measurement apparatus according to claim 1, wherein the approximate feature portion or the detailed feature portion is on a boundary or an edge of a part to be measured, or in a vicinity thereof.

6. An image measurement apparatus according to claim 1, further comprising:

a laser scanner which has the distance-angle measurement block for measuring the distance to and the angle of a point contained in the first image;

wherein distance information at each point is handled as color information of the first image, in accordance with laser light emitted from the laser scanner and reflected by the object; intensity information of the reflected laser light is handled as the first image; or internal luminance information is handled as the first image.

7. An image measurement apparatus according to claim 1, wherein the distance-angle measurement block is further for measuring the distance to and the angle of the position of the detailed feature portion obtained from the super-resolution image.

8. An image measurement apparatus according to claim 1, wherein the measurement processing block specifies an image acquisition range to be measured by the measuring apparatus;

the measurement processing block obtains images in the range while making micro-movements;

the measurement processing block uses the measuring apparatus to perform distance-angle measurement or three-dimensional measurement of the image acquisition position;

the orthoimage creation block creates orthoimages of the obtained images;

the feature extraction processing block extracts a feature portion from each of the obtained images;

the partial-image creation processing block creates a partial image of the feature portion extracted by the feature extraction processing block;

the super-resolution-image creation processing block creates a super-resolution image;

the feature extraction processing block extracts a feature again from the super-resolution image created by the super-resolution-image creation processing block; and the result of feature extraction is stored in a storage block or output to an output block.

9. An image measurement apparatus according to claim 1, wherein the measurement processing block obtains a plurality of images to be measured by a measuring apparatus;

the feature extraction processing block extracts a feature portion from each of the plurality of images obtained;

the partial-image creation processing block creates a partial image of each feature portion;

the super-resolution-image creation processing block creates a super-resolution image;

the feature extraction processing block extracts a feature portion again from the image subjected to the super-resolution processing; and the result of feature extraction is stored in a storage block or output to an output block.

* * * * *

UNITED STATES PATENT AND TRADEMARK OFFICE
CERTIFICATE OF CORRECTION

PATENT NO. : 8,300,986 B2  
APPLICATION NO. : 12/186893  
DATED : October 30, 2012  
INVENTOR(S) : Nobuo Kochi et al.

Page 1 of 1

It is certified that error appears in the above-identified patent and that said Letters Patent is hereby corrected as shown below:

ON THE FRONT PAGE – The Foreign Application Priority Data should read:

(30)   The Foreign Application Priority Data:

August 29, 2007    (JP)    2007-222002

Signed and Sealed this  
Fifth Day of February, 2013

Teresa Stanek Rea  
*Acting Director of the United States Patent and Trademark Office*